United States Patent
Herold et al.

(10) Patent No.: US 7,718,675 B2
(45) Date of Patent: *May 18, 2010

(54) DIAMINO ALCOHOLS AND THEIR USE AS RENIN INHIBITOR

(75) Inventors: Peter Herold, Basel (CH); Stefan Stutz, Basel (CH); Aleksandar Stojanovic, Basel (CH); Vincenzo Tschinke, Binningen (CH); Christiane Marti, Baden (CH); Michael Quirmbach, Basel (CH)

(73) Assignee: Speedel Experimenta AG, Allschwil (CH)

( * ) Notice: Subject to any disclaimer, the term of this patent is extended or adjusted under 35 U.S.C. 154(b) by 701 days.

This patent is subject to a terminal disclaimer.

(21) Appl. No.: 10/586,814

(22) PCT Filed: Jan. 21, 2005

(86) PCT No.: PCT/EP2005/050272

§ 371 (c)(1),
(2), (4) Date: Jul. 24, 2006

(87) PCT Pub. No.: WO2005/070877

PCT Pub. Date: Aug. 4, 2005

(65) Prior Publication Data

US 2007/0161622 A1     Jul. 12, 2007

(30) Foreign Application Priority Data

Jan. 23, 2004     (CH) .................................... 0094/04

(51) Int. Cl.
A61K 31/445     (2006.01)
C07D 211/06     (2006.01)
(52) U.S. Cl. ................. 514/331; 546/184; 546/192; 546/229; 546/232; 514/315; 514/317; 544/106; 544/358
(58) Field of Classification Search ............... 546/184, 546/192, 229, 232; 544/106, 358; 514/231.2, 514/252.12, 315, 317, 331
See application file for complete search history.

(56) References Cited

U.S. PATENT DOCUMENTS

| 5,194,608 | A | 3/1993 | Toyoda et al. |
| 5,223,615 | A | 6/1993 | Toyoda et al. |
| 5,272,268 | A | 12/1993 | Toyoda et al. |
| 6,887,863 | B2 * | 5/2005 | Craig et al. ............... 514/183 |
| 7,312,360 | B2 * | 12/2007 | TenBrink et al. ............ 564/185 |
| 2004/0044072 | A1 | 3/2004 | TenBrink et al. |

FOREIGN PATENT DOCUMENTS

| EP | 0 468 641 | 1/1992 |
| WO | 03/050073 | 6/2003 |

OTHER PUBLICATIONS

J.M. Wood et al., "Structure-based design of aliskiren, a novel orally effective renin inhibitor", Biochemical and Biophysical Research Communications, Academic Press Inc., vol. 308, No. 4, pp. 698-705, XP004447169, ISSN: 0006-291X, Sep. 5, 2003.
K. Allikmets, "Aliskiren Speedel", Current Opinion in Investigational Drugs, Pharmapress, U.S., vol. 3, No. 10, pp. 1479-1482, XP009017210, ISSN: 1472-4472, 2002.
P. Raddatz et al., "Renin Inhibitors Containing New P1-P1' Dipeptide Mimetics with Heterocycles in P1'", Journal of Medicinal Chemistry, American Chemical Society, vol. 35, No. 19, pp. 3525-3536, XP002050635, ISSN: 0022-2623, Sep. 18, 1992.

* cited by examiner

*Primary Examiner*—Golam M Shameem
(74) *Attorney, Agent, or Firm*—Wenderoth, Lind & Ponack, L.L.P.

(57) ABSTRACT

The application relates to novel amino alcohols of the general formula (I) where R, $R_1$, $R_2$, $R_3$, $R_4$, $R_5$ and $R_6$ each have the definitions illustrated in detail in the description, to a process for their preparation, and to the use of these compounds as medicines, in particular as renin inhibitors.

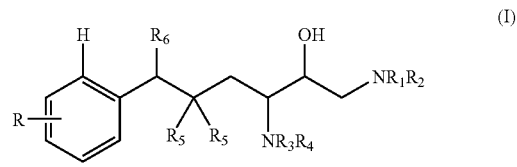

9 Claims, No Drawings

DIAMINO ALCOHOLS AND THEIR USE AS RENIN INHIBITOR

The invention relates to novel amino alcohols, to processes for preparing the inventive compounds, to pharmaceutical preparations comprising them and to their use as active ingredients in medicaments, in particular as renin inhibitors.

Amino-compounds showing renin-inhibiting properties are known, for example from EP519433.

Firstly, the present invention provides compounds of the general formula (I)

where
$R_1$ is
a) hydrogen, hydroxyl or amino; or
b) $C_1$-$C_8$-alkyl, $C_3$-$C_8$-cycloalkyl, $C_1$-$C_8$-alkanoyl, $C_1$-$C_8$-alkoxycarbonyl, aryl-$C_0$-$C_4$-alkyl or heterocyclyl-$C_0$-$C_4$-alkyl, which radicals may be substituted by 1-4 $C_1$-$C_8$-alkyl, halogen, oxo, cyano, trifluoromethyl, $C_1$-$C_8$-alkoxy, $C_1$-$C_8$-alkoxycarbonyl, aryl or heterocyclyl;

$R_2$ is
a) $C_1$-$C_8$-alkyl, $C_3$-$C_8$-cycloalkyl, $C_1$-$C_8$-alkylsulphonyl, $C_3$-$C_8$-cycloalkylsulphonyl, aryl-$C_0$-$C_8$-alkylsulphonyl, heterocyclylsulphonyl, $C_3$-$C_{12}$-cycloalkyl-$C_1$-$C_8$-alkanoyl, aryl-$C_1$-$C_8$-alkanoyl, aryl-$C_3$-$C_8$-cycloalkanoyl, $C_1$-$C_8$-alkanoyl, $C_1$-$C_8$-alkoxycarbonyl, optionally N-mono- or N,N-di-$C_1$-$C_8$-alkylated carbamoyl-$C_0$-$C_8$-alkyl, aryl-$C_0$-$C_4$-alkyl or heterocyclyl-$C_0$-$C_4$-alkyl, which radicals may be substituted by 1-4 $C_1$-$C_8$-alkyl, $C_3$-$C_8$-cycloalkyl, $C_3$-$C_8$-cycloalkoxy, amino, $C_{1-6}$-alkylamino, di-$C_{1-6}$-alkylamino, $C_1$-$C_6$-alkanoylamino, $C_1$-$C_8$-alkoxy-carbonylamino, halogen, oxo, cyano, hydroxyl, trifluoromethyl, $C_1$-$C_8$-alkoxy, $C_1$-$C_8$-alkoxycarbonyl, aryl or heterocyclyl; or
b) together with $R_1$ and the nitrogen atom to which they are bonded is a saturated or partly unsaturated, 4-8-membered, heterocyclic ring which may contain an additional nitrogen, oxygen or sulphur atom or an —SO— or —SO2-group, and the additional nitrogen atom may optionally be substituted by $C_1$-$C_8$-alkyl, $C_1$-$C_8$-alkanoyl, $C_1$-$C_8$-alkoxycarbonyl, aryl or heteroaryl radicals, in which case this heterocyclic ring may be part of a bicyclic or tricyclic ring system having a total of up to 16 members and the second ring may also contain a nitrogen, oxygen or sulphur atom or an —SO— or —SO2-group, and the nitrogen atom of the second ring may optionally be substituted by $C_1$-$C_8$-alkyl, $C_1$-$C_8$-alkanoyl, $C_1$-$C_8$-alkoxy-carbonyl, aryl or heterocyclyl radicals, and all ring systems mentioned may be substituted by 1-4 $C_1$-$C_8$-alkyl, halogen, hydroxyl, oxo, trifluoromethyl, $C_1$-$C_8$-alkoxy, $C_1$-$C_8$-alkoxy-$C_1$-$C_8$-alkyl, $C_1$-$C_8$-alkoxy-$C_1$-$C_8$-alkoxy, $C_1$-$C_8$-alkoxycarbonylamino, $C_1$-$C_8$-alkanoylamino, $C_1$-$C_8$-alkylamino, N,N-di-$C_1$-$C_8$-alkylamino, aryl-$C_0$-$C_4$-alkyl, aryloxy-$C_0$-$C_4$-alkyl, aryl-$C_0$-$C_4$-alkyl-$C_1$-$C_8$-alkoxy, aryloxy-$C_0$-$C_4$-alkyl-$C_1$-$C_8$-alkoxy, heterocyclyl-$C_0$-$C_4$-alkyl, heterocyclyloxy-$C_0$-$C_4$-alkyl, heteroaryl-$C_0$-$C_4$-alkyl-$C_1$-$C_8$-alkoxy or heterocyclyloxy-$C_0$-$C_4$-alkyl-$C_1$-$C_8$-alkoxy;

$R_3$ is hydrogen, $C_1$-$C_4$-alkyl, $C_1$-$C_8$-alkoxycarbonyl or $C_1$-$C_8$-alkanoyl;

$R_4$ is hydrogen, $C_1$-$C_4$-alkyl, $C_1$-$C_8$-alkoxycarbonyl or $C_1$-$C_8$-alkanoyl;

$R_5$ is in each case independently hydrogen, $C_1$-$C_8$-alkyl, or, together with the carbon atom to which they are bonded, are a $C_3$-$C_6$-cycloalkylidene radical;

$R_6$ is hydrogen or hydroxyl;

R, in each case independently, are 1-4 radicals selected from: hydrogen, halogen, $C_1$-$C_8$-alkyl, 3- to 8-membered cycloalkyl, polyhalo-$C_1$-$C_4$-alkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, 3- to 8-membered cycloalkoxy-$C_1$-$C_4$-alkyl, hydroxyl, $C_1$-$C_8$-alkanoyloxy-$C_1$-$C_4$-alkyl, hydroxy-$C_2$-$C_8$-alkyl, $C_1$-$C_4$-alkylthio-$C_1$-$C_4$-alkyl, $C_1$-$C_8$-alkylsulphonyl-$C_1$-$C_4$-alkyl, thiazolylthio-$C_1$-$C_4$-alkyl, thiazolinylthio-$C_1$-$C_4$-alkyl, imidazolylthio-$C_1$-$C_4$-alkyl, optionally N-oxidized pyridylthio-$C_1$-$C_4$-alkyl, pyrimidinylthio-$C_1$-$C_4$-alkyl, optionally partially hydrogenated pyridyl- or N-oxidopyridyl-$C_1$-$C_4$-alkyl, $C_1$-$C_4$-alkylsulphonylamino-$C_1$-$C_4$-alkyl, trifluoro-$C_1$-$C_8$-alkylsulphonyl-amino-$C_1$-$C_4$-alkyl, pyrrolidino-$C_1$-$C_4$-alkyl, piperidino-$C_1$-$C_4$-alkyl, piperazino-$C_1$-$C_4$-alkyl, N'-$C_1$-$C_4$-alkylpiperazino-$C_1$-$C_4$-alkyl, N'-$C_2$-$C_8$-alkanoylpiperazino-$C_1$-$C_4$-alkyl, morpholino-$C_1$-$C_4$-alkyl, thiomorpholino-$C_1$-$C_4$-alkyl, S-oxothiomorpholino-$C_1$-$C_4$-alkyl, S,S-dioxothiomorpholino-$C_1$-$C_4$-alkyl, cyano-$C_1$-$C_4$-alkyl, carboxy-$C_1$-$C_4$-alkyl, $C_1$-$C_4$-alkoxy-carbonyl-$C_1$-$C_4$-alkyl, carbamoyl-$C_1$-$C_8$-alkyl, N-mono- or N,N-di-$C_1$-$C_4$-alkylcarbamoyl-$C_1$-$C_4$-alkyl, unsubstituted or mono-, di- or tri-$C_1$-$C_4$-alkyl-, —$C_1$-$C_4$-alkoxy-, -hydroxy-, —$C_1$-$C_4$-alkylamino-, -di-$C_1$-$C_4$-alkylamino-, -halogen- or -trifluoromethyl-substituted phenyl or naphthyl, hydroxy-$C_2$-$C_8$-alkoxy, halo-$C_2$-$C_8$-(hydroxy)alkoxy, $C_1$-$C_8$-alkylsulphonyl-$C_1$-$C_4$-(hydroxy)-alkoxy, amino-$C_1$-$C_4$-alkyl, $C_1$-$C_4$-alkylamino-$C_1$-$C_4$-alkyl, N,N-di-$C_1$-$C_4$-alkylamino-$C_1$-$C_4$-alkyl, N—$C_1$-$C_4$-alkanoylamino-$C_1$-$C_4$-alkyl, $C_1$-$C_8$-alkoxycarbonylamino-$C_1$-$C_4$-alkyl, optionally partially hydrogenated pyridyl- or N-oxidopyridyl-$C_1$-$C_4$-alkyl, piperazino-$C_1$-$C_4$-alkyl, N'-$C_1$-$C_4$-alkylpiperazino-$C_1$-$C_4$-alkyl, N'-$C_2$-$C_8$-alkanoylpiperazino-$C_1$-$C_4$-alkyl, morpholino-$C_1$-$C_4$-alkyl, thiomorpholino-$C_1$-$C_4$-alkyl, S-oxothiomorpholino-$C_1$-$C_4$-alkyl, S,S-dioxothiomorpholino-$C_1$-$C_4$-alkyl, amino-$C_1$-$C_4$-alkoxy, $C_1$-$C_4$-alkylamino-$C_1$-$C_4$-alkoxy, N,N-di-$C_1$-$C_4$-alkylamino-$C_1$-$C_4$-alkoxy, $C_1$-$C_4$-alkanoylamino-$C_1$-$C_4$-alkoxy, $C_1$-$C_8$-alkoxycarbonylamino-$C_1$-$C_4$-alkoxy, $C_1$-$C_8$-alkanoyl-$C_2$-$C_4$-alkoxy which bears the alkanoyl group in a position higher than the α-position, $C_1$-$C_8$-alkoxy, 3- to 8-membered cycloalkoxy, $C_2$-$C_8$-alkenyloxy, 3- to 8-membered cycloalkoxy-$C_1$-$C_4$-alkoxy, $C_1$-$C_8$-alkoxy-$C_1$-$C_8$-alkoxy, $C_1$-$C_4$-alkoxy-$C_2$-$C_4$-alkenyl, $C_2$-$C_8$-alkenyloxy-$C_1$-$C_4$-alkoxy, $C_1$-$C_4$-alkoxy-$C_2$-$C_4$-alkenyloxy, $C_2$-$C_8$-alkenyloxy-$C_1$-$C_4$-alkyl, $C_1$-$C_4$-alkylthio-$C_1$-$C_4$-alkoxy, $C_1$-$C_8$-alkylsulphonyl-$C_1$-$C_4$-alkoxy, $C_1$-$C_4$-alkylthio-$C_1$-$C_4$-(hydroxy)alkoxy, unsubstituted or mono-, di- or tri-$C_1$-$C_4$-alkyl-, —$C_1$-$C_4$-alkoxy-, -hydroxy-, —$C_1$-$C_4$-alkylamino-, -di-$C_1$-$C_4$-alkylamino-, -halo- and/or -trifluoromethyl-substituted phenyl- or naphthyl-$C_1$-$C_4$-alkoxy, polyhalo-$C_1$-$C_4$-alkoxy, optionally partially hydogenated pyridyl- or N-oxidopyridyl-$C_1$-$C_4$-alkoxy, thiazolyl-$C_1$-$C_4$-alkoxy, optionally N-oxidized morpholino-$C_1$-$C_4$-alkoxy, thiazolylthio-$C_1$-$C_4$-alkoxy, thiazolinylthio-$C_1$-$C_4$-alkoxy, imidazolylthio-$C_1$-$C_4$-alkoxy, optionally N-oxidized pyridylthio-$C_1$-$C_4$-alkoxy, pyrimidinylthio-$C_1$-$C_4$-alkoxy, amino-$C_1$-$C_4$-alkoxy, $C_1$-$C_4$-alkylamino-$C_1$-$C_4$-alkoxy, N,N-di-$C_1$-$C_4$-alkylamino-$C_1$-$C_4$-alkoxy, $C_1$-$C_8$-alkanoylamino-$C_1$-$C_4$-alkoxy, $C_1$-$C_8$-alkylsulphonylamino-$C_1$-$C_4$-alkoxy, trifluoro-$C_1$-$C_8$-alkylsulphonyl-$C_1$-$C_4$-alkoxy, pyrrolidino-$C_1$-$C_4$-alkoxy, piperidino-$C_1$-$C_4$-alkoxy, cyano-$C_1$-$C_4$-alkoxy, carboxy-$C_1$-$C_4$-alkoxy, $C_1$-$C_4$-alkoxycarbonyl-$C_1$-$C_4$-alkoxy, carbamoyl-$C_1$-$C_4$-alkoxy, N—$C_1$-$C_8$-alkylcarbamoyl-$C_1$-$C_4$-alkoxy or N-mono- or N,N-di-$C_1$-$C_4$-alkylcarbamoyl-$C_1$-$C_4$-alkoxy, carboxy-$C_1$-$C_4$-alkyl, $C_1$-$C_4$-alkoxycarbonyl-$C_1$-$C_4$-alkyl, carbamoyl-$C_1$-$C_8$-alkyl, N-mono- or N,N-di-$C_1$-$C_4$-alkylcarbamoyl-$C_1$-$C_4$-alkyl, carboxy-$C_1$-$C_4$-alkoxy, $C_1$-$C_4$-alkoxycarbonyl-$C_1$-$C_4$-alkoxy, carbamoyl-$C_1$-$C_8$-alkoxy, N-Mono- or N,N-di-$C_1$-$C_4$-alkylcarbamoyl-$C_1$-$C_4$-alkoxy, $C_1$-$C_4$-alkylamino or N,N-di-$C_1$-$C_4$-alkylamino, and salts thereof, preferably pharmaceutically usable salts thereof.

Aryl, and aryl in, for example, aryl-$C_0$-$C_4$-alkyl, aryloxy-$C_0$-$C_4$-alkyl, aryl-$C_0$-$C_4$-alkyl-$C_1$-$C_8$-alkoxy, aryloxy-$C_0$-$C_4$-alkyl-$C_1$-$C_8$-alkoxy, aryl-$C_3$-$C_8$-cycloalkanoyl, aryl-$C_1$-$C_8$-alkanoyl and aryl-$C_0$-$C_8$-alkylsulphonyl, contains generally 1-14, preferably 6-10 carbon atoms, and is, for example, phenyl, indenyl, e.g. 2- or 4-indenyl, or naphthyl, e.g. 1- or 2-naphthyl. Preference is given to aryl having 6-10 carbon atoms, in particular phenyl or 1- or 2-naphthyl. The radicals mentioned may be unsubstituted or mono- or polysubstituted, for example mono- or disubstituted, for example by $C_1$-$C_8$-alkyl, $C_3$-$C_8$-cycloalkyl, $C_3$-$C_8$-cycloalkoxy, amino, $C_{1-6}$-alkylamino, di-$C_{1-6}$-alkylamino, $C_0$-$C_6$-alkylcarbonylamino, halogen, oxo, cyano, hydroxyl, trifluoromethyl, $C_1$-$C_8$-alkoxy, $C_1$-$C_8$-alkoxycarbonyl, aryl or heterocyclyl, and the substituent may be in any position, for example in the o-, m- or p-position of the phenyl radical, or in the 3- or 4-position of the 1- or 2-naphthyl radical, and a plurality of identical or different substituents may also be present.

Aryl-$C_0$-$C_4$-alkyl is, for example, phenyl, naphthyl or benzyl.

Aryl-$C_0$-$C_8$-alkylsulphonyl is one of the aryl radicals mentioned which is bonded to the rest of the compound either via a sulphonyl group or via a $C_1$-$C_8$-alkylsulphonyl group, for example phenylsulphonyl, benzylsulphonyl or phenyldimethylenesulphonyl.

Heterocyclyl contains generally from 4 to 8, in particular from 5 to 7, ring atoms, and may also have 1 or 2 fused-on phenyl or cycloalkyl radicals, or else be present as a spiro compound. Examples include pyrrolidino, piperidino, pyridinyl, piperazino, morpholino, thiomorpholino, furanyl, tetrahydrofuranyl, pyranyl, tetrahydropyranyl, thiazolyl, oxazolyl, imidazolyl, indolinyl, isoindolinyl, 2,3-dihydrobenzimidazolyl, 1,2,3,4-tetrahydroquinolyl, 1,2,3,4-tetrahydroisoquinolyl, 1,2,3,4-tetrahydro-1,3-benzodiazinyl, 1,2,3,4-tetrahydro-1,4-benzodiazinyl, 3,4-dihydro-2H-1,4-benzoxazinyl, 3,4-dihydro-2H-1,4-benzothiazinyl, 3,4-dihydro-2H-1,3-benzothiazinyl, 3,4,5,6,7,8-hexahydro-2H-1,4-benzoxazinyl, 3,4,5,6,7,8-hexahydro-2H-1,4-benzothiazinyl, 9-azabicyclo[3.3.1]non-9-yl, 1-azepan-1-yl, 2,8-diazaspiro[4.5]dec-8-yl, octahydroisoindol-2-yl, 4-azatricyclo[5.2.1.0$^{2,6}$]dec-4-yl, 3-azabicyclo[3.2.1]oct-3-yl, 3,7-diazabicyclo[3.3.1]non-3-yl, 3-azabicyclo[3.3.1]non-3-yl, 8-azabicyclo[3.2.1]oct-8-yl, 3-azabicyclo[3.2.2]non-3-yl, 2,3,4,5-tetrahydro-1H-1-benz[6,7-b]azepinyl and 5,6-dihydrophenanthridinyl. The radicals mentioned may be unsubstituted or N-substituted and/or C-substituted, in which case in particular 1, 2 or 3 substituents may be present.

In the case of nitrogen heterocycles, the heterocyclyl radicals may be bonded either via the nitrogen or via a ring carbon.

Heterocyclylsulphonyl is one of the heterocyclyl radicals mentioned which is bonded to the rest of the compound via a sulphonyl group.

Halogen is, for example, fluorine, chlorine, bromine or iodine, preferably fluorine and chlorine.

Carbamoyl-$C_0$-$C_8$-alkyl is, for example, carbamoyl, carbamoylmethyl, 2-carbamoylethyl, 3-carbamoylpropyl, 2-(3-carbamoyl)propyl, 2-carbamoylpropyl, 3-(1-carbamoyl)propyl, 2-(2-carbamoyl)propyl, 2-carbamoyl-2-methylpropyl, 4-carbamoylbutyl, 1-carbamoylbutyl, 1-(1-carbamoyl-2-methyl)butyl, 3-(4-carbamoyl-2-methyl)butyl.

3- to 8-membered cycloalkoxy is preferably 3-, 5- or 6-membered cycloalkoxy, such as cyclopropyloxy, cyclopentyloxy, cyclohexyloxy.

3- to 8-membered cycloalkyl is preferably 3-, 5- or 6-membered cycloalkyl, such as cyclopropyl, cyclopentyl, cyclohexyl.

$C_3$-$C_{12}$-cycloalkyl-$C_1$-$C_8$-alkanoyl is one of the cycloalkyl radicals mentioned which is bonded to the rest of the compound via a $C_1$-$C_8$-alkanoyl group, for example adamantylformyl, cyclobutylformyl, cyclopentylformyl, cyclohexylformyl, cyclohexyl-acetyl, 2-cyclopentyl-2-methylpropionyl, 2-cyclohexylpropionyl, 3-cyclohexylpropionyl or 2-cyclohexyl-2-methyl-propionyl.

$C_3$-$C_8$-cycloalkylsulphonyl is, for example, cyclopentylsulphonyl, cyclohexylsulphonyl or cycloheptylsulphonyl, and also cyclopropylsulphonyl, cyclobutylsulphonyl or cyclooctylsulphonyl.

N,N-di-$C_1$-$C_6$-alkylamino is, for example, dimethylamino, N-methyl-N-ethylamino, diethylamino, N-methyl-N-propylamino or N-butyl-N-methylamino.

N,N-di-$C_1$-$C_8$-alkylcarbamoyl-$C_0$-$C_8$-alkyl is, for example, carbamoyl, 2-dimethylcarbamoyl-ethyl, 3-dimethylcarbamoylpropyl, 2-dimethylcarbamoylpropyl, 2-(dimethylcarbamoyl)-2-methylpropyl or 2-(1-dimethylcarbamoyl)-3-methylbutyl.

$C_1$-$C_8$-alkanoyl is in particular $C_2$-$C_6$-alkanoyl, such as acetyl, propionyl, butyryl, isobutyryl or pivaloyl.

$C_1$-$C_6$-alkanoylamino is, for example, formylamino, acetylamino or pivaloylamino.

$C_1$-$C_6$-alkylamino is, for example, $C_1$-$C_4$-alkylamino, such as methylamino, ethylamino, propylamino, butylamino, isobutylamino, sec-butylamino or tert-butylamino.

$C_1$-$C_8$-alkylcarbamoyl-$C_0$-$C_8$-alkyl is, for example, N—$C_1$-$C_8$-alkylcarbamoyl-$C_1$-$C_4$-alkyl, such as methyl- or dimethylcarbamoyl-$C_1$-$C_4$-alkyl, for example methylcarbamoylmethyl, 2-methylcarbamoylethyl, 3-methylcarbamoylpropyl or in particular 2-methylcarbamoyl-2-methylpropyl.

$C_1$-$C_8$-alkoxy is, for example, $C_1$-$C_5$-alkoxy, such as methoxy, ethoxy, propyloxy, isopropyloxy, butyloxy, isobutyloxy, sec-butyloxy, tert-butyloxy or pentyloxy, but may also be a hexyloxy or heptyloxy group.

$C_1$-$C_8$-alkoxycarbonyl is preferably $C_2$-$C_5$-alkoxycarbonyl, such as methoxycarbonyl, ethoxycarbonyl, propyloxycarbonyl, isopropyloxycarbonyl, butyloxycarbonyl, isobutyloxycarbonyl, sec-butyloxycarbonyl or tert-butyloxycarbonyl.

$C_1$-$C_8$-alkoxy-$C_1$-$C_8$-alkoxy is, for example, 2-methoxy-, 2-ethoxy- or 2-propyloxyethoxy, 3-methoxy- or 3-ethoxypropyloxy or 4-methoxybutyloxy, in particular 3-methoxypropyloxy or 4-methoxybutyloxy.

$C_1$-$C_4$-alkoxy-$C_1$-$C_4$-alkoxy-$C_1$-$C_4$-alkyl is, for example, $C_1$-$C_4$-alkoxy-$C_1$-$C_4$-alkoxy-$C_1$-$C_4$-alkyl, such as 2-methoxy-, 2-ethoxy- or 2-propyloxyethoxymethyl, 2-(2-methoxy-, 2-ethoxy- or 2-propyloxyethoxy)ethyl, 3-(3-methoxy- or 3-ethoxypropyloxy)propyl or 4-(2-methoxybutyloxy)butyl, in particular 2-(3-methoxypropyloxy)ethyl or 2-(4-methoxybutyloxy)ethyl.

$C_1$-$C_8$-alkoxy-$C_1$-$C_8$-alkyl is, for example, ethoxymethyl, propyloxymethyl, butyloxymethyl, 2-methoxy-, 2-ethoxy- or 2-propyloxyethyl, 3-methoxy- or 3-ethoxypropyl or 4-methoxybutyl, in particular 3-methoxypropyl or 4-methoxybutyl.

$C_1$-$C_8$-alkyl may be straight-chain or branched, and is, for example, methyl, ethyl, propyl, isopropyl, butyl, isobutyl, sec-butyl, tert-butyl, or a pentyl, hexyl or heptyl group.

$C_1$-$C_8$-alkylsulphonyl is, for example, methylsulphonyl, ethylsulphonyl, propylsulphonyl, isopropylsulphonyl, butylsulphonyl, isobutylsulphonyl, sec-butylsulphonyl, tert-butylsulphonyl, or a pentyl-, hexyl-, heptyl- or octylsulphonyl group.

Depending on the presence of asymmetric carbon atoms, the inventive compounds may be present in the form of isomer mixtures, especially as racemates, or in the form of pure isomers, especially of optical antipodes.

Salts of compounds having salt-forming groups are in particular acid addition salts, salts with bases or, in the presence of a plurality of salt-forming groups, in some cases also mixed salts or internal salts.

Salts are primarily the pharmaceutically usable or nontoxic salts of compounds of the formula I.

Such salts are formed, for example, from compounds of the formula I with an acidic group, for example a carboxyl or sulpho group, and are, for example, the salts thereof with suitable bases, such as nontoxic metal salts derived from metals of group Ia, Ib, IIa and IIb of the Periodic Table of the Elements, for example alkali metal, in particular lithium, sodium or potassium salts, alkaline earth metal salts, for example magnesium or calcium salts, and also zinc salts or ammonium salts, including those salts which are formed with organic amines, such as optionally hydroxy-substituted mono-, di- or trialkylamines, in particular mono-, di- or tri(lower alkyl)amines, or with quaternary ammonium bases, for example methyl-, ethyl-, diethyl- or triethylamine, mono-, bis- or tris(2-hydroxy(lower alkyl))amines, such as ethanol-, diethanol- or triethanolamine, tris(hydroxymethyl)methylamine or 2-hydroxy-tert-butylamine, N,N-di(lower alkyl)-N-(hydroxy(lower alkyl))amine, such as N,N-di-N-dimethyl-N-(2-hydroxy-ethyl)amine, or N-methyl-D-glucamine, or quaternary ammonium hydroxides, such as tert-butylammonium hydroxide. The compounds of the formula I having a basic group, for example an amino group, may form acid addition salts, for example with suitable inorganic acids, e.g. hydrohalic acid such as hydrochloric acid, hydrobromic acid, sulphuric acid with replacement of one or both protons, phosphoric acid with replacement of one or more protons, e.g. orthophosphoric acid or metaphosphoric acid, or pyrophosphoric acid with replacement of one or more protons, or with organic carboxylic, sulphonic, sulpho or phosphonic acids or N-substituted sulphamic acids, e.g. acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid, isonicotinic acid, and also amino acids, for example the α-amino acids mentioned above, and also methanesulphonic acid, ethanesulphonic acid, 2-hydroxyethanesulphonic acid, ethane-1,2-disulphonic acid, benzenesulphonic acid, 4-toluenesulphonic acid, naphthalene-2-sulphonic acid, 2- or 3-phosphoglycerate, glucose 6-phosphate, N-cyclohexylsulphamic acid (with formation of cyclamates) or with other acidic organic compounds such as ascorbic acid. Compounds of the formula I with acidic and basic groups may also form internal salts.

For the isolation and purification, pharmaceutically unsuitable salts may also find use.

Prodrug derivatives of the compounds described in the present context are derivatives thereof which, on in vivo application, release the original compound by a chemical or physiological process. A prodrug may be converted to the original compound, for example, when a physiological pH is attained or by enzymatic conversion. Prodrug derivatives may, for example, be esters of freely available carboxylic acids, S- and O-acyl derivatives of thiols, alcohols or phenols, and the acyl group is as defined in the present context. Preference is given to pharmaceutically usable ester derivatives which are converted by solvolysis in physiological medium to the original carboxylic acid, for example lower alkyl esters, cycloalkyl esters, lower alkenyl esters, benzyl esters, mono- or disubstituted lower alkyl esters such as lower ω-amino, mono- or dialkylamino, carboxyl, lower alkoxycarbonyl)-alkyl esters or such as lower α-(alkanoyloxy, alkoxycarbonyl or dialkylaminocarbonyl)-alkyl esters; as such, pivaloyloxymethyl esters and similar esters are utilized in a conventional manner.

Owing to the close relationship between a free compound, a prodrug derivative and a salt compound, a certain compound in this invention also encompasses its prodrug derivative and salt form, where these are possible and appropriate.

The compounds of the formula (I) also include those compounds in which one or more atoms are replaced by their stable, non-radioactive isotopes; for example, a hydrogen atom by deuterium.

The compounds of the formula (I) and their pharmaceutically usable salts have inhibiting action on the natural enzyme renin. The latter passes from the kidneys into the blood and there brings about the cleavage of angiotensinogen to form the decapeptide angiotensin I which is then cleaved in the lung, the kidneys and other organs to the octapeptide angiotensin II. Angiotensin II increases the blood pressure both directly by arterial constriction and indirectly by the hormone aldosterone which inhibits the release of the sodium ion from the adrenal glands, which is associated with a rise in the extracellular liquid volume. This rise can be attributed to the action of angiotensin II itself or of the heptapeptide angiotensin III formed therefrom as a cleavage product. Inhibitors of the enzymatic activity of renin bring about a reduction in the formation of angiotensin I and, as a consequence thereof, the formation of a smaller amount of angiotensin II. The reduced concentration of this active peptide hormone is the immediate cause of the hypotensive action of renin inhibitors.

One experimental method of detecting the action of renin inhibitors is by means of in vitro tests, in which the reduction of the formation of angiotensin I in different systems (human plasma, purified human renin together with synthetic or natural renin substrate) is measured. One in vitro test which is used is the one according to Nussberger et al. (1987) J. Cardiovascular Pharmacol., Vol. 9, p. 39-44 which follows. This test measures the formation of angiotensin I in human plasma. The amount of angiotensin I formed is determined in a subsequent radioimmunoassay. Which action inhibitors have on the formation of angiotensin I is tested in this system by the addition of different concentrations of these substances. The $IC_{50}$ refers to that concentration of the particular inhibitor which reduces the formation of angiotensin I by 50%. The compounds of the present invention exhibit inhibiting actions in the in vitro systems at minimum concentrations of about $10^{-6}$ to about $10^{-10}$ mol/l.

In salt-depleted animals, renin inhibitors bring about a blood pressure decrease. Human renin differs from renin of other species. To test inhibitors of human renin, primates (marmosets, *Callithrixjacchus*) are used, because human renin and primate renin are substantially homologous in the enzymatically active region. One in vivo test which is used is as follows: the test compounds are tested on normotensive marmosets of both genders and having a body weight of about 350 g which are conscious, able to move freely and in their normal cages. Blood pressure and heart rate are measured using a catheter in the descending aorta and recorded radiometrically. The endogenous release of renin is stimulated by the combination of a 1-week low-salt diet with a single intramuscular injection of furosemide (5-(aminosulphonyl)-4-chloro-2-[(2-furanylmethyl)amino]benzoic acid) (5 mg/kg). 16 hours after the injection of furosemide, the test substances are administered either directly into the femoral artery by means of an injection cannula or into the stomach by gavage as a suspension or solution, and their effect on blood pressure and heart rate was evaluated. The compounds of the present invention effectively reduce blood pressure in the in vivo test described at doses of about 0.003 to about 0.3 mg/kg i.v. and at doses of about 0.3 to about 30 mg/kg p.o.

The compounds of the present invention may find use for the treatment of hypertension, congestive heart failure, cardiac hypertrophy, cardiac fibrosis, cardiomyopathy postinfarction, complications resulting from diabetes, such as nephropathy, vasculopathy and neuropathy, disorders of the cardiac vessel, restenosis after angioplasty, increased intraocular pressure, glaucoma, abnormal vascular growth, hyperaldosteronism, states of anxiety and cognitive disorders.

The compound groups mentioned below are not to be regarded as closed, but rather parts of these compound groups may be exchanged with one another or with the definitions given above or omitted in a sensible manner, for example to replace general by more specific definitions.

The invention relates preferably to compounds of the formula I where $R_1$ is
a) hydrogen; or
b) $C_1$-$C_8$-alkyl or $C_3$-$C_8$-cycloalkyl;

$R_2$ is
a) $C_1$-$C_8$-alkyl, $C_3$-$C_8$-cycloalkyl, $C_1$-$C_8$-alkanoyl, heterocyclyl-$C_1$-$C_8$-alkanoyl, $C_3$-$C_{12}$-cycloalkyl-$C_1$-$C_8$-alkanoyl or aryl-$C_1$-$C_8$-alkanoyl, which radicals may be substituted by 1-4 $C_1$-$C_8$-alkyl, $C_{1-6}$-alkylamino, cyano, halogen, hydroxyl, $C_1$-$C_6$-alkanoylamino, $C_1$-$C_8$-alkoxycarbonylamino, $C_1$-$C_8$-alkoxy, oxo, trifluoromethyl or aryl; or
b) together with $R_1$ and the nitrogen atom to which they are bonded are a saturated or partly unsaturated, 4-8-membered, heterocyclic ring which may contain an additional nitrogen or oxygen atom, in which case the additional nitrogen atom may optionally be substituted by $C_1$-$C_8$-alkyl or $C_1$-$C_8$-alkanoyl, and this heterocyclic ring may be part of a bicyclic or tricyclic ring system having a total of up to 16 ring members and the second ring may also contain a nitrogen or oxygen atom, in which case the nitrogen atom of the second ring may optionally be substituted by $C_1$-$C_8$-alkyl or $C_1$-$C_8$-alkanoyl, and all ring systems mentioned may be substituted by 1-4 $C_1$-$C_8$-alkyl, hydroxyl, oxo, $C_1$-$C_8$-alkoxy, $C_1$-$C_8$-alkoxy-$C_1$-$C_8$-alkoxy, $C_1$-$C_8$-alkanoylamino, $C_1$-$C_8$-alkoxycarbonylamino or aryloxy-$C_0$-$C_4$-alkyl-$C_1$-$C_8$-alkoxy;

$R_3$ is hydrogen;
$R_4$ is hydrogen;
$R_5$ are each independently hydrogen or $C_1$-$C_8$-alkyl;
$R_6$ is hydrogen;
R are each independently 1-4 radicals selected from:
hydrogen, $C_1$-$C_8$-alkyl, halogen, trifluoromethyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_8$-alkoxy, $C_1$-$C_4$-alkoxy-$C_1$-$C_4$-alkoxy,
and pharmaceutically usable salts thereof.

Particular preference is given in each case to those compounds of the formula I where at least one, for example one, two or preferably all three, asymmetric carbon atoms of the main chain have the stereochemistry (in each case "S") shown in the formula Ia

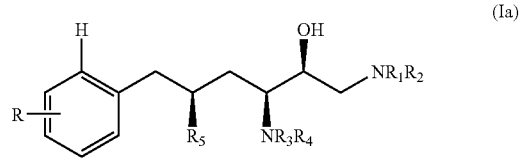

where the substituents are each as defined above, and pharmaceutically usable salts thereof.

The compounds of the formula (I) may also be prepared in optically pure form. The separation into antipodes may be effected by methods known per se, either preferably at a synthetically earlier stage by salt formation with an optically active acid, for example (+)- or (−) mandelic acid and separation of the diastereomeric salts by fractional crystallization, or preferably at a rather later stage by derivatization with a chiral auxiliary building block, for example (+)- or (−)-camphanoyl chloride, and separation of the diastereomeric products by chromatography and/or crystallization and subsequent cleavage of the bond to the chiral auxiliary. To determine the absolute configuration of the piperidine present, the pure diastereomeric salts and derivatives may be analysed with common spectroscopic methods, of which X-ray spectroscopy on single crystals constitutes a particularly suitable method.

The compounds of the formula (I) or formula (Ia), and their pharmaceutically usable salts may find use as medicines, for example in the form of pharmaceutical preparations. The pharmaceutical preparations may be administered enterally, such as orally, for example in the form of tablets, coated tablets, sugar-coated tablets, hard and soft gelatine capsules, solutions, emulsions or suspensions, nasally, for example in the form of nasal sprays, rectally, for example in the form of suppositories, or transdermally, for example in the form of ointments or patches. The administration may also be parenteral, such as intramuscular or intravenous, for example in the form of injection solutions.

To prepare tablets, coated tablets, sugar-coated tablets and hard gelatine capsules, the compounds of the formula (I) or formula (Ia), and pharmaceutically usable salts thereof, may be processed with pharmaceutically inert, inorganic or organic excipients. Such excipients used, for example for tablets, coated tablets and hard gelatine capsules, may be lactose, corn starch, or derivatives thereof, talc, stearic acid or salts thereof etc.

Suitable excipients for soft gelatine capsules are, for example, vegetable oils, waxes, fats, semisolid and liquid polyols, etc.

Suitable excipients for preparing solutions and syrups are, for example, water, polyols, sucrose, invert sugar, glucose, etc.

Suitable excipients for injection solutions are, for example, water, alcohols, polyols, glycerol, vegetable oils, bile acids, lecithin, etc.

Suitable excipients for suppositories are, for example, natural or hardened oils, waxes, fats, semisolid or liquid polyols, etc.

The pharmaceutical preparations may additionally also comprise preservatives, solubilizers, viscosity-increasing substances, stabilizers, wetting agents, emulsifiers, sweeteners, colorants, flavourings, salts for altering the osmotic pressure, buffers, coatings or antioxidants. They may also comprise other therapeutically valuable substances.

The present invention further provides the use of the compounds of the formula (I) or formula (Ia), and the pharmaceutically usable salts thereof, in the treatment or prevention of hypertension and heart failure, and also glaucoma, cardiac infarction, kidney failure and restenoses.

The compounds of the formula (I) or formula (Ia), and the pharmaceutically usable salts thereof, may also be administered in combination with one or more agents having cardiovascular action, for example α- and β-blockers such as phentolamine, phenoxy-benzamine, prazosin, terazosin, tolazine, atenolol, metoprolol, nadolol, propranolol, timolol, carteolol etc.; vasodilators such as hydralazine, minoxidil, diazoxide, nitroprusside, flosequinan etc.; calcium antagonists such as amrinone, bencyclan, diltiazem, fendiline, flunarizine, nicardipine, nimodipine, perhexilene, verapamil, gallopamil, nifedipine etc.; ACE inhibitors such as cilazapril, captopril, enalapril, lisinopril etc.; potassium activators such as pinacidil; anti-serotoninergics such as ketanserin; thromboxane synthetase inhibitors; neutral endopeptidase inhibitors (NEP inhibitors); angiotensin II antagonists; and also diuretics such as hydrochlorothiazide, chlorothiazide, acetazolamide, amiloride, bumetanide, benzthiazide, ethacrynic acid, furosemide, indacrinone, metolazone, spironolactone, triamteren, chlorthalidone etc.; sympatholytics such as methyldopa, clonidine, guanabenz, reserpine; and other agents which are suitable for the treatment of hypertension, heart failure or vascular diseases in humans and animals which are associated with diabetes or renal disorders such as acute or chronic renal failure. Such combinations may be employed separately or in preparations which comprise a plurality of components.

Further substances which can be used in combination with the compounds of the formulae (I) and (Ia) are the compounds of classes (i) to (ix) on page 1 of WO 02/40007 (and also the preferences and examples further listed therein) and the substances specified on pages 20 and 21 of WO 03/027091.

The dose may vary within wide limits and has of course to be adapted to the individual circumstances in each individual case. In general, for oral administration, a daily dose of about 3 mg to about 3 g, preferably about 10 mg to about 1 g, for example about 300 mg, per adult (70 kg), divided into preferably 1-3 individual doses which may, for example, be of equal size, may be appropriate, although the upper limit specified may also be exceeded if this should be found to be appropriate; typically, children receive a lower dose according to their age and body weight.

The compounds of the formula (I) or formula (Ia) may be prepared in an analogous manner to preparative processes known from the literature. The starting materials to carry out the preparative processes are described, for example, in EP 0678503. The inventive compounds of the formula I and salts of such compounds having at least one salt-forming group are obtained by processes known per se, for example by a) condensing a compound of the formula II

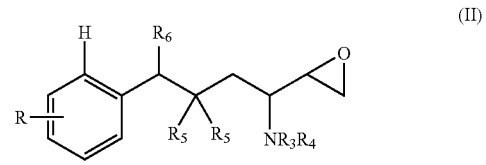

where R, $R_3$, $R_4$, $R_5$ and $R_6$ are each as defined above or a salt thereof with a compound of the formula $R_1R_2NH$ (III) where $R_1$ and $R_2$ are each as defined above, in the course of which free functional groups in the reaction components with the exception of the groups taking part in the reaction are present in protected form, and detaching protecting groups present. In cases where $R_1$ and $R_2$ are a saturated or partly unsaturated oxo-substituted heterocyclic ring (for example lactams) and strong bases are used as a reagent, the alkoxide formed by epoxide opening may react with one of the protecting groups present (e.g. N-Boc) and form an oxazolidinone which may be cleaved to give the product, for example with lithium hydroxide, or b) condensing a compound of the formula II

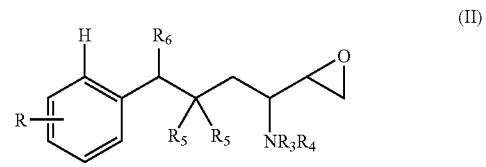

where R, $R_3$, $R_4$, $R_5$ and $R_6$ are each as defined above or a salt thereof with an azide, reducing the azido group to amino and then, depending on the definitions of $R_1$ and $R_2$, mono- or dialkylating, mono- or diacylating, and also optionally sulphonylating the amino group, in the course of which free functional groups present in the reaction components with the exception of the groups taking part in the reaction are present in protected form, and detaching protecting groups present, or c) condensing a compound of the formula IV

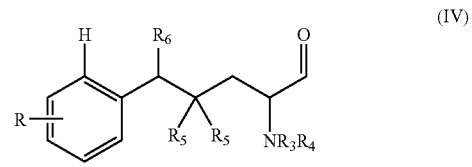

where R, $R_3$, $R_4$, $R_5$ and $R_6$ are each as defined above or a salt thereof with cyanide or nitromethane, reducing the nitrile group or nitro group to amino, and then, depending on the definitions of $R_1$ and $R_2$, mono- or dialkylating, mono- or diacylating, and also optionally sulphonylating the amino group, in the course of which free functional groups present in the reaction components with the exception of the groups taking part in the reaction are present in protected form, and detaching protecting groups present.

Compounds of the formula II can be prepared in an analogous manner to preparative processes known from the literature, for example by a) condensing a compound of the formula IV

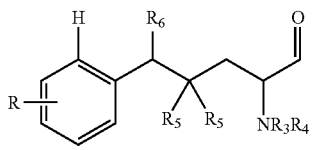

(IV)

where R, $R_3$, $R_4$, $R_5$ and $R_6$ are each as defined above or a salt thereof with methylide (see, for example, in Tet. Lett. 30(40), 5425-5428, 1989), in the course of which free functional groups present in the reaction components with the exception of the groups taking part in the reaction are present in protected form, and detaching protecting groups present, or b) epoxidizing a compound of the formula V

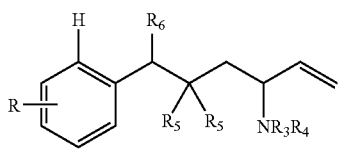

(V)

where R, $R_3$, $R_4$, $R_5$ and $R_6$ are each as defined above or a salt thereof (see, for example, in J. Med. Chem. 35(10), 1685-1701, 1992 and J. Org. Chem. 59(3), 653-657, 1994), in the course of which free functional groups present in the reaction components with the exception of the groups taking part in the reaction are present in protected form, and protecting groups present are detached, or c) dihydroxylating a compound of the formula V

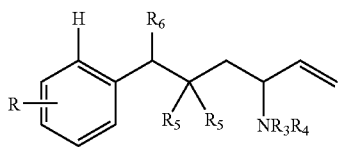

(V)

where R, $R_3$, $R_4$, $R_5$ and $R_6$ are each as defined above or a salt thereof, tosylating the primary alcohol and subsequently admixing with a base such as potassium hydroxide (see, for example in WO 03050073), in the course of which free functional groups present in the reaction components with the exception of the groups taking part in the reaction are present in protected form, and detaching protecting groups present, or d) preparing an activated ester from a compound of the formula VI

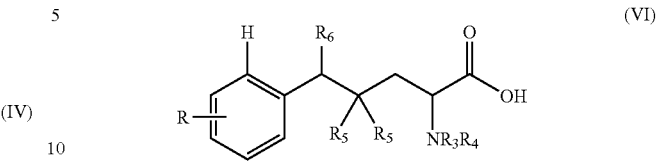

where R, $R_3$, $R_4$, $R_5$ and $R_6$ are each as defined above or a salt thereof and admixing it with diazomethane, admixing the diazoketone with 48% HBr, and then reducing the bromoketone and subsequently admixing it with a base such as potassium hydroxide (see, for example, in WO 03050073), in the course of which free functional groups present in the reaction components with the exception of the groups taking part in the reaction are present in protected form, and detaching protecting groups present.

Details of the specific preparation variants can be taken from the examples.

The examples which follow illustrate the present invention. All temperatures are reported in degrees Celsius, pressures in mbar. Unless stated otherwise, the reactions take place at room temperature. The abbreviation "Rf=xx (A)" means, for example, that the Rf value xx is determined in the solvent system A. The ratio of solvents relative to one another is always reported in parts by volume. Chemical names for end products and intermediates were generated with the aid of the program AutoNom 2000 (automatic nomenclature).

Thin-film chromatography eluent systems:

A  dichloromethane-methanol-25% conc. ammonia=200:20:1

B  dichloromethane-methanol-25% conc. ammonia=40:10:1

C  dichloromethane-methanol-25% conc. ammonia=200:10:1

D  dichloromethane-methanol-25% conc. ammonia=

E  dichloromethane-methanol-water-conc. acetic acid=150:54:10:1

HPLC gradients on Hypersil BDS C-18 (5 um); column: 4×125 mm

I  90% water*/10% acetonitrile* to 0% water*/100% acetonitrile* in 5 minutes+2.5 minutes (1.5 ml/min)

II  95% water*/5% acetonitrile* to 0% water*/100% acetonitrile* in 40 minutes (0.8 m/min)

*: containing 0.1% trifluoroacetic acid

The following abbreviations are used:

Rf ratio of distance traveled by a substance to separation of the eluent front from the start point in thin-film chromatography Rt retention time of a substance in HPLC (in minutes)

m.p. melting point (temperature)

General Method A: (N-BOC Deprotection)

A solution of 0.2 mmol of "N-BOC derivative" in 2 ml of 4N HCl/dioxane is stirred at 0° C. over 2-6 hours. The reaction mixture is admixed with dioxane, frozen in liquid nitrogen and lyophilized under high vacuum overnight. The title compound is obtained from the residue.

EXAMPLE 1

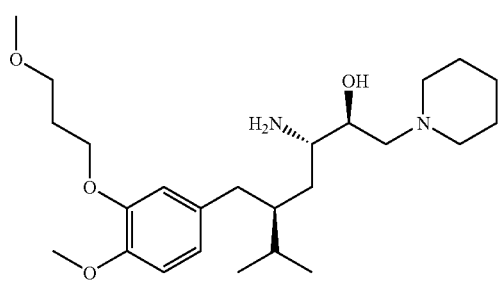

3(S)-Amino-5(S)-[4-methoxy-3-(3-methoxypropoxy)benzyl]-6-methyl-1-piperidin-1-yl-heptan-2(S)-ol dihydrochloride Analogously to method A, 0.255 g of tert-butyl {1(S)-(1(S)-hydroxy-2-piperidin-1-ylethyl)-3(S)-[4-methoxy-3-(3-methoxypropoxy)benzyl]-4-methylpentyl}carbamate is used to prepare the title compound.

The starting materials are prepared as follows:

a) tert-Butyl {1(S)-(1(S)-hydroxy-2-piperidin-1-ylethyl)-3(S)-[4-methoxy-3-(3-methoxypropoxy)benzyl]-4-methylpentyl}carbamate A solution of 0.25 g of tert-butyl {3(S)-[4-methoxy-3-(3-methoxypropoxy)benzyl]-4-methyl-1(S)-(R)-oxiranylpentyl}carbamate in 4 ml of isopropanol and 0.99 ml of piperidine is stirred at 70° C. over 1 hour. The reaction mixture is concentrated by evaporation, and the residue is admixed with water and extracted with tert-butyl methyl ether (2×). The combined organic phases are washed with water and brine, dried over sodium sulphate and concentrated by evaporation. The title compound is obtained from the residue by means of flash chromatography (SiO2 60F) as a colourless oil. Rf=0.24 (9:1 dichloromethane-methanol); Rt=17.40 (gradient II).

b) tert-Butyl {3(S)-[4-methoxy-3-(3-methoxypropoxy)benzyl]-4-methyl-1(S)-(R)-oxiranylpentyl}carbamate 3.87 g of trimethylsulphoxonium iodide and 1.98 g of potassium tert-butoxide are stirred under high vacuum overnight, admixed with 24 ml of tetrahydrofuran and subsequently cooled to 0° C. A solution of 4.00 g of tert-butyl {1(S)-formyl-3(S)-[4-methoxy-3-(3-methoxypropoxy)benzyl]4-methylpentyl}carbamate [CAS 172900-83-3] in 24 ml of dimethyl sulphoxide is added dropwise. After 2 hours, the reaction mixture is partitioned between water and tert-butyl methyl ether and the aqueous phase is extracted once more with tert-butyl methyl ether (2×). The combined organic phases are washed successively with water (3×) and brine, dried over sodium sulphate and concentrated by evaporation. The title compound is obtained from the residue first by means of flash chromatography (SiO2 60F) and then by means of crystallization (hexane) as white crystals. Rf=0.43 (1:1 EtOAc-heptane); Rt=21.90 (gradient II); m.p. 59-65° C.

EXAMPLE 2

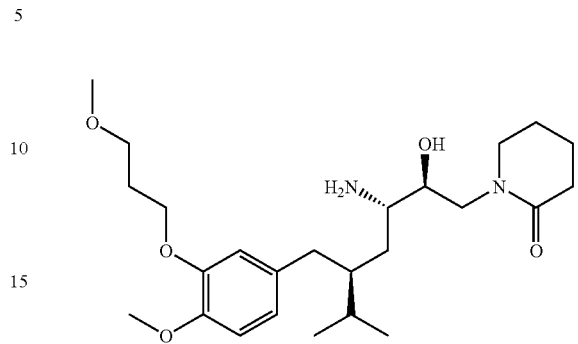

1-{3(S)-Amino-2(S)-hydroxy-5(S)-[4-methoxy-3-(3-methoxypropoxy)benzyl]-methylheptyl}piperidin-2-one hydrochloride A solution of 0.050 g of 1-(4(S)-{2(S)-[4-methoxy-3-(3-methoxypropoxy)benzyl]-3-methylbutyl}2-oxooxazolidin-5(S)-ylmethyl)piperidin-2-one and 0.050 g of lithium hydroxide hydrate in 1.5 ml of ethanol and 1.5 ml of water is stirred at 100° C. over 2 hours. The reaction mixture is cooled to room temperature, poured onto ice-water and extracted with ethyl acetate (3×). The combined organic phases are dried over sodium sulphate and concentrated by evaporation. The title compound is obtained from the residue by means of flash chromatography (SiO2 60F) as the free base. This is dissolved in 0.5 ml of dioxane, admixed with 20 µl of 4N HCl/dioxane, frozen in liquid nitrogen and lyophilized under high vacuum overnight. The title compound is obtained from the residue.

The starting materials are prepared as follows:

a) 1-(4(S)-{2(S)-[4-Methoxy-3-(3-methoxypropoxy)benzyl]-3-methylbutyl}-2-oxooxazolidin-5(S)-ylmethyl)piperidin-2-one A mixture of 0.115 g of piperidin-2-one and 0.136 g of potassium tert-butoxide in 3 ml of dimethyl sulphoxide is stirred at room temperature over 30 minutes, admixed with 0.25 g of tert-butyl {3(S)-[4-methoxy-3-(3-methoxypropoxy)benzyl]-4-methyl-1(S)-(R)-oxiranylpentyl}carbamate (font size changed from Arial 10 to 11) (Example 1b) and subsequently stirred further at room temperature overnight. The reaction mixture is poured onto ice-water and extracted with tert-butyl methyl ether (2×). The combined organic phases are washed successively with water and brine, dried over sodium sulphate and concentrated by evaporation. The title compound is obtained from the residue by means of flash chromatography (SiO2 60F) as a yellow oil. Rf=0.33 (95:5 dichloromethane-methanol); Rt=3.94 (gradient I).

According to the processes described in Examples 1 and 2, the following compounds are prepared in an analogous manner:

Examples:
3  3(S)-amino-1-(cis-2,6-dimethylpiperidin-1-yl)-5(S)-[4-methoxy-3-(3-methoxypropoxy)benzyl]-6-methylheptan-2(S)-ol dihydrochloride
4 1-{3(S)-amino-2(S)-hydroxy-5(S)-[4-methoxy-3-(3-methoxypropoxy)benzyl]-6-methylheptyl}pyrrolidin-3(S)-ol dihydrochloride 5 1-{3(S)-amino-2(S)-hydroxy-5(S)-[4-methoxy-3-(3-methoxypropoxy)benzyl]-6-methylheptyl}pyrrolidin-3(R)-ol dihydrochloride 6 N-(1-{3(S)amino-2(S)-hydroxy-5-[4-methoxy-3-(3-methoxypropoxy)benzyl]-6-methylheptyl}pyrrolidin-3(S)-yl)acetamide hydrochloride 7 N-(1-{3(S)-amino-2(S)-hydroxy-5(S)-[4-methoxy-3-(3-methoxypropoxy)benzyl]-6-methylheptyl}pyrrolidin-3(R)-yl)acetamide hydrochloride 8 3(S)-amino-5(S)-[4-methoxy-3-(3-methoxypropoxy)benzyl]-6-methyl-1-morpholin-4-ylheptan-2(S)-ol dihydrochloride 9 3(S)-amino-1-azepan-1-yl-5(S)-[4-methoxy-3-(3-methoxypropoxy)benzyl]-6-methylheptan-2(S)-ol dihydrochloride 10 1-{3(S)-amino-2(S)-hydroxy-5(S)-[4-methoxy-3-(3-methoxypropoxy)benzyl]-6-methylheptyl}azepan-2-one hydrochloride 11 3(S)-amino-5(S)-[4-methoxy-3-(3-methoxypropoxy)benzyl]-6-methyl-1-(2(S)-methylpiperidin-1-yl)heptan-2(S)-ol dihydrochloride 12 3(S)-amino-5(S)-[4-methoxy-3-(3-methoxypropoxy)benzyl]-6-methyl-1-(2(R)-methylpiperidin-1-yl)heptan-2(S)-ol dihydrochloride 13 3(S)-amino-5(S)-[4-methoxy-3-(3-methoxypropoxy)benzyl]-6-methyl-1-(3(R,S)-methylpiperidin-1-yl)heptan-2(S)-ol dihydrochloride 14 3(S)-amino-5(S)-[4-methoxy-3-(3-methoxypropoxy)benzyl]-6-methyl-1-(4-methylpiperidin-1-yl)heptan-2(S)-ol dihydrochloride 15 3(S)-amino-5(S)-[4-methoxy-3-(3-methoxypropoxy)benzyl]-1-(3(S)-methoxypyrrolidin-1-yl)-6-methylheptan-2(S)-ol dihydrochloride 16 3(S)-amino-5(S)-[4-methoxy-3-(3-methoxypropoxy)benzyl]-1-(3(R)-methoxypyrrolidin-1-yl)-6-methylheptan-2(S)-ol dihydrochloride 17 3(S)-amino-1-dimethylamino-5(S)-[4-methoxy-3-(3-methoxypropoxy)benzyl]-6-methylheptan-2(S)-ol dihydrochloride 18 3(S)-amino-1-isobutylamino-5(S)-[4-methoxy-3-(3-methoxypropoxy)benzyl]-6-methylheptan-2(S)-ol dihydrochloride 19 3(S)-amino-1-azetidin-1-yl-5(S)-[4-methoxy-3-(3-methoxypropoxy)benzyl]-6-methylheptan-2(S)-ol dihydrochloride 20 3(S)-amino-1-benzylamino-5(S)-[4-methoxy-3-(3-methoxypropoxy)benzyl]-6-methylheptan-2(S)-ol dihydrochloride 21 3(S)-amino-1-(benzylmethylamino)-5(S)-[4-methoxy-3-(3-methoxypropoxy)benzyl]-6-methylheptan-2(S)-ol dihydrochloride 22 3(S)-amino-(S)-[4-methoxy-3-(3-methoxypropoxy)benzyl]-6-methyl-1-pyrrolidin-1-ylheptan-2(S)-ol dihydrochloride 23 3(S)-amino-1-isopropylamino-5(S)-[4-methoxy-3-(3-methoxypropoxy)benzyl]-6-methylheptan-2(S)-ol dihydrochloride 24 3(S)-amino-1-cyclopropylamino-5(S)-[4-methoxy-3-(3-methoxypropoxy)benzyl]-6-methylheptan-2(S)-ol dihydrochloride 25 3(S)-amino-1-ethylamino-5(S)-[4-methoxy-3-(3-methoxypropoxy)benzyl]-6-methylheptan-2(S)-ol dihydrochloride 26 3(S)-amino-1-diethylamino-5(S)-[4-methoxy-3-(3-methoxypropoxy)benzyl]-6-methylheptan-2(S)-ol dihydrochloride 27 3(S)-amino-1-tert-butylamino-5(S)-[4-methoxy-3-(3-methoxypropoxy)benzyl]-6-methylheptan-2(S)-ol dihydrochloride 28 3(S)-amino-1-cyclopentylamino-5(S)-[4-methoxy-3-(3-methoxypropoxy)benzyl]-6-methylheptan-2(S)-ol dihydrochloride 29 3(S)-amino-5(S)-[4-methoxy-3-(3-methoxypropoxy)benzyl]-6-methyl-1-propylaminoheptan-2(S)-ol dihydrochloride 30 3(S)-amino-1-(isopropylmethylamino)-5(S)-[4-methoxy-3-(3-methoxypropoxy)benzyl]-6-methylheptan-2(S)-ol dihydrochloride 31 3(S)-amino-1-(1-ethylpropylamino)-5(S)-[4-methoxy-3-(3-methoxypropoxy)benzyl]-6-methylheptan-2(S)-ol dihydrochloride 32 3(S)-amino-1-(benzylisopropylamino)-5(S)-[4-methoxy-3-(3-methoxypropoxy)benzyl]-6-methylheptan-2(S)-ol dihydrochloride 33 3(S)-amino-1-(cyclopropylmethylamino)-5(S)-[4-methoxy-3-(3-methoxypropoxy)benzyl]-6-methylheptan-2(S)-ol dihydrochloride 35 3(S)-amino-1-[isopropyl-(2-methoxyethyl)amino]-5(S)-[4-methoxy-3-(3-methoxypropoxy)benzyl]-6-methylheptan-2(S)-ol dihydrochloride 37 3(S)-amino-5(S)-[4-methoxy-3-(3-methoxypropoxy)benzyl]-6-methyl-1-(2(S)-trifluoromethylpyrrolidin-1-yl)heptan-2(S)-ol dihydrochloride 40 3(S)-amino-1-(2(R)-ethylpyrrolidin-1-yl)-5(S)-[4-methoxy-3-(3-methoxypropoxy)benzyl]-6-methylheptan-2(S)-ol dihydrochloride 41 3(S)-amino-1-((S)-sec-butylamino)-5(S)-[4-methoxy-3-(3-methoxypropoxy)benzyl]-6-methylheptan-2(S)-ol dihydrochloride 42 3(S)-amino-1((R)-sec-butylamino)-5(S)-[4-methoxy-3-(3-methoxypropoxy)benzyl]-6-methylheptan-2(S)-ol dihydrochloride 43 3(S)-amino-5(S)-[4-methoxy-3-(3-methoxypropoxy)benzyl]-6-methyl-1-(1(R)-methylpentylamino)heptan-2(S)-ol dihydrochloride 44 3(S)-amino-5(S)-[4-methoxy-3-(3-methoxypropoxy)benzyl]-6-methyl-1-(1(S)-methylpentylamino)heptan-2(S)-ol dihydrochloride 45 3(S)-amino-5(S)-[4-methoxy-3-(3-methoxypropoxy)benzyl]-6-methyl-1-(1(S)-methylhexylamino)heptan-2(S)-ol dihydrochloride 46 3(S)-amino-5(S)-[4-methoxy-3-(3-methoxypropoxy)benzyl]-1-(2S)-methoxymethylpyrrolidin-1-yl)-6-methylheptan-2(S)-ol dihydrochloride 47 3(S)-amino-5(S)-[4-methoxy-3-(3-methoxypropoxy)benzyl]-1-(2R)-methoxymethylpyrrolidin-1-yl)-6-methylheptan-2(S)-ol dihydrochloride 48 3(S)-amino-5(S)-[4-methoxy-3-(3-methoxypropoxy)benzyl]-6-methyl-1-(1(R)-methylhexylamino)heptan-2(S)-ol dihydrochloride 49 3(S)-amino-5(S)-[4-methoxy-3-(3-methoxypropoxy)benzyl]-6-methyl-1-(2(R)-propylpyrrolidin-1-yl)heptan-2(S)-ol dihydrochloride 55 3(S)-amino-5(S)-[4-methoxy-3-(3-methoxypropoxy)benzyl]-6-methyl-1-(thiazol-2-ylamino)heptan-2(S)-ol hydrochloride 57 2(S)-{3(S)-amino-2(S)-hydroxy-5(S)-[4-methoxy-3-(3-methoxypropoxy)benzyl]-6-methylheptylamino}propionamide dihydrochloride 58 2-{3(S)-amino-2(S)-hydroxy-5(S)-[4-methoxy-3-(3-methoxypropoxy)benzyl]-6-methylheptylamino}acetamide dihydrochloride 77  3(S)-amino-1-(1,1-dimethylpropylamino)-5(S)-[4-methoxy-3-(3-methoxypropoxy)benzyl]-6-methylheptan-2(S)-ol dihydrochloride 78  3(S)-amino-1-(1-ethyl-1-methylpropylamino)-5(S)-[4-methoxy-3-(3-methoxypropoxy)benzyl]-6-methylheptan-2(S)-ol dihydrochloride

EXAMPLE 34

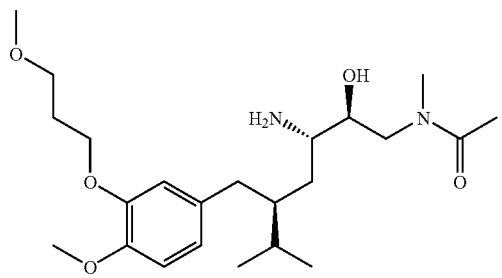

N-{3(S)-Amino-2(S)-hydroxy-5(S)-[4-methoxy-3-(3-methoxypropoxy)benzyl]-6-methylheptyl}-N-methylacetamide hydrochloride Analogously to method A, 0.050 g of tert-butyl {1(S)-[2-(acetylmethylamino)-1(S)-hydroxyethyl]-3(S)-[4-methoxy-3-(3-methoxypropoxy)benzyl]-4-methylpentyl}carbamate is used to prepare the title compound.

The starting material is prepared as follows:

a) tert-Butyl {1(S)-[2-(acetylmethylamino)-1(S)-hydroxyethyl]-3(S)-[4-methoxy-3-(3-methoxypropoxy)benzyl]-4-methylpentyl}carbamate A solution of 0.050 g of tert-butyl {3(S)-[4-methoxy-3-(3-methoxypropoxy)benzyl]-4-methyl-1(S)-(R)-oxiranylpentyl}carbamate (Example 1b) in 1.0 ml of isopropanol and 0.10 ml of methylamine is stirred at 60° C. over 2 hours. The reaction mixture is concentrated by evaporation to dryness. The residue is dissolved in 2 ml of dichloromethane, admixed successively with 0.017 ml of pyridine and 0.026 ml of acetic anhydride and stirred at room temperature over 1 hour. The reaction solution is admixed with water and extracted with tert-butyl methyl ether (2×). The combined organic phases are washed successively with 1M HCl, water and brine, dried over sodium sulphate and concentrated by evaporation. The title compound is obtained from the residue by means of flash chromatography (SiO2 60F) as a slightly yellowish oil. Rf=0.13 (95:5 dichloromethane-methanol); Rt=4.47 (gradient I).

EXAMPLE 36

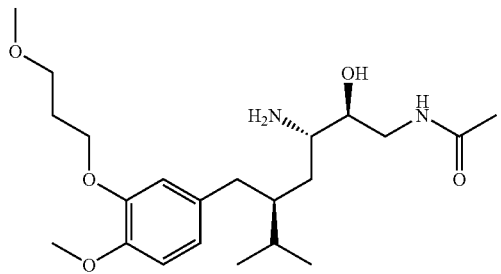

N-{3(S)-Amino-2(S)-hydroxy-5(S)-[4-methoxy-3-(3-methoxypropoxy)benzyl]-6-methylheptyl}acetamide hydrochloride Analogously to method A, 0.026 g of tert-butyl {1(S)-(2-acetylamino-1(S)-hydroxyethyl)-3(S)-[4-methoxy-3-(3-methoxypropoxy)benzyl]-4-methylpentyl}carbamate is used to prepare the title compound.

The starting materials are prepared as follows:

a) tert-Butyl {1(S)-(2-acetylamino-1(S)-hydroxyethyl)-3(S)-[4-methoxy-3-(3-methoxypropoxy)benzyl]-4-methylpentyl}carbamate The solution of 0.040 g of tert-butyl {1(S)-(2-amino-1(S)-hydroxyethyl)-3(S)-[4-methoxy-3-(3-methoxypropoxy)benzyl]-4-methylpentyl}carbamate in 2 ml of dichloromethane is admixed successively with 0.007 ml of pyridine and 0.011 ml of acetic anhydride and stirred at room temperature over 1 hour. The reaction solution is admixed with water and extracted with tert-butyl methyl ether (2×). The combined organic phases are washed with 1M HCl, water and brine, dried over sodium sulphate and concentrated by evaporation. The title compound is obtained from the residue by means of flash chromatography (SiO2 60F) as a colourless oil. Rf=0.37 (200:20:1 dichloromethane-methanol-25% conc. ammonia); Rt=17.25 (gradient II).

b) tert-Butyl {1(S)-(2-amino-1(S)-hydroxyethyl)-3(S)-[4-methoxy-3-(3-methoxypropoxy)benzyl]-4-methylpentyl}carbamate The solution of 0.185 g of tert-butyl {1(S)-(2-azido-1(S)-hydroxyethyl)-3(S)-[4-methoxy-3-(3-methoxypropoxy)benzyl]-4-methylpentyl}carbamate in 6 ml of methanol is hydrogenated in the presence of 0.037 g of 10% Pd/C over 2 hours. The reaction mixture is clarified by filtration and concentrated by evaporation. The title compound is obtained from the residue by means of flash chromatography (SiO2 60F) as a slightly greyish oil. Rf=0.08 (200:20:1 dichloromethane-methanol-25% conc. ammonia); Rt=15.47 (gradient II).

c) tert-Butyl {1(S)-(2-azido-1(S)-hydroxyethyl)-3(S)-[4-methoxy-3-(3-methoxypropoxy)benzyl]-4-methylpentyl}carbamate The solution of 3.10 g of tert-butyl {3(S)-[4-methoxy-3-(3-methoxypropoxy)benzyl]4-methyl-1(S)-(R)-oxiranylpentyl}carbamate (Example 1b) in 64 ml of methanol is admixed with 1.04 g of sodium azide and 0.62 g of ammonium chloride and stirred at reflux over 6 hours. The reaction solution is cooled, poured onto ice-water and extracted with tert-butyl methyl ether (2×). The combined organic phases are washed successively with water and brine, dried over sodium sulphate and concentrated by evaporation. The title compound is obtained from the residue by means of flash chromatography (SiO2 60F) and subsequent crystallization (diisopropyl ether) as white crystals. Rf=0.29 (1:2 EtOAc-heptane); Rt=21.60 (gradient II). m.p. 98-99° C.

EXAMPLE 39

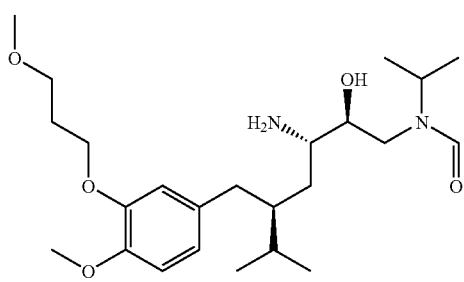

N-{3(S)-Amino-2(S)-hydroxy-5(S)-[4-methoxy-3-(3-methoxypropoxy)benzyl]-6-methylheptyl}-N-isopropylformamide hydrochloride Analogously to method A 0.031 g of tert-butyl {1(S)-[2-(formylisopropylamino)-1(S)-hydroxyethyl]-3(S)-[4-methoxy-3-(3-methoxypropoxy)benzyl]-4-methylpentyl}carbamate is used to prepare the title compound.

The starting material is prepared as follows:

a) tert-Butyl {1(S)-[2-(formylisopropylamino)-1(S)-hydroxyethyl]-3(S)-[4-methoxy-3-(3-methoxypropoxy)benzyl]-4-methylpentyl}carbamate A solution of 0.030 g of tert-butyl {3(S)-[4-methoxy-3-(3-methoxypropoxy)benzyl]-4-methyl-1(S)-(R)-oxiranylpentyl}carbamate (Example 1b) in 1.0 ml of isopropanol and 0.165 ml of isopropylamine is stirred at 60° C. over 2 hours. The reaction mixture is concentrated by evaporation to dryness. The residue is dissolved in 1.22 ml of dichloromethane, admixed successively with 0.006 ml of pyridine and 0.013 g of 4-nitrophenyl formate and stirred at room temperature over 1 hour. The reaction solution is admixed with water and extracted with tert-butyl methyl ether (2×). The combined organic phases are washed with 1M HCl, water and brine, dried over sodium sulphate and concentrated by evaporation. The title compound is obtained from the residue by means of flash chromatography (SiO2 60F) as a slightly yellowish oil. Rf=0.51 (95:5 dichloromethane-methanol).

EXAMPLE 51

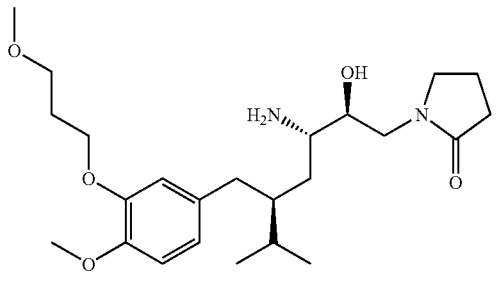

1-{3(S)-Amino-2(S)-hydroxy-5(S)-[4-methoxy-3-(3-methoxypropoxy)benzyl]-6-methylheptyl}pyrrolidin-2-one hydrochloride Analogously to method A 0.028 g of tert-butyl {1(S)-[1(S)-hydroxy-2-(2-oxopyrrolidin-1-yl)ethyl]-3(S)-[4-methoxy-3-(3-methoxypropoxy)benzyl]-4-methylpentyl}carbamate is used to prepare the title compound.

The starting material is prepared as follows:

a) tert-Butyl {1(S)-[1(S)-hydroxy-2-(2-oxopyrrolidin-1-yl)ethyl]-3(S)-[4-methoxy-3-(3-methoxypropoxy)benzyl]-4-methylpentyl}carbamate A solution of 0.025 g of tert-butyl {3(S)-[4-methoxy-3-(3-methoxypropoxy)benzyl]-4-methyl-1(S)-(R)-oxiranylpentyl}carbamate (Example 1b) in 0.50 ml of isopropanol is admixed successively with 0.027 g of 4-aminobutyric acid and 0.13 ml of 1M NaOH and stirred at 60° C. over 3 hours. The reaction mixture is cooled to 0° C. and admixed with 0.13 ml of 1M HCl and concentrated by evaporation to dryness. The residue is dissolved in 2.5 ml of dichloromethane, admixed successively with 0.016 g of N,N-dicyclohexylcarbodiimide and 0.012 mg of 1-hydroxybenzotriazole, and stirred at room temperature over 18 hours. The reaction solution is admixed with 1M sodium hydrogen carbonate solution and extracted with ethyl acetate (2×). The combined organic phases are washed with brine, dried over sodium sulphate and concentrated by evaporation. The title compound is obtained from the residue by means of flash chromatography (SiO2 60F) as a colourless oil. Rf=0.32 (200:20:1 dichloromethane-methanol-25% conc. ammonia); Rt=4.51 (gradient I).

EXAMPLE 52

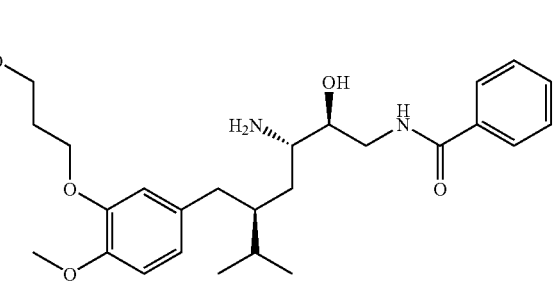

N-{3(S)-Amino-2(S)-hydroxy-5(S)-[4-methoxy-3-(3-methoxypropoxy)benzyl]-6-methylheptyl}benzamide hydrochloride Analogously to method A 0.025 g of tert-butyl {1(S)-(2-benzoylamino-1(S)-hydroxyethyl)-3(S)-[4-methoxy-3-(3-methoxypropoxy)benzyl]-4-methylpentyl}carbamate is used to prepare the title compound.

The starting material is prepared as follows:

a) tert-Butyl {1(S)-(2-benzoylamino-1(S)-hydroxyethyl)-3(S)-[4-methoxy-3-(3-methoxypropoxy)benzyl]-4-methylpentyl}carbamate The solution of 0.025 g of tert-butyl {1(S)-(2-amino-1(S)-hydroxyethyl)-3(S)-[4-methoxy-3-(3-methoxypropoxy)benzyl]-4-methylpentyl}carbamate (Example 36b) and 0.8 ml of dichloromethane is admixed successively with 0.006 ml of triethylamine and 0.007 ml of benzoyl chloride and stirred at room temperature over 1 hour. The reaction solution is admixed with water and extracted with tert-butyl methyl ether (2×). The combined organic phases are washed successively with water and brine, dried over sodium sulphate and concentrated by evaporation. The title compound is obtained from the residue by means of flash chromatography (SiO2 60F) as a colourless oil. Rf=0.74 (200:20:1 dichloromethane-methanol-25% conc. ammonia); Rt=5.01 (gradient I).

EXAMPLE 56

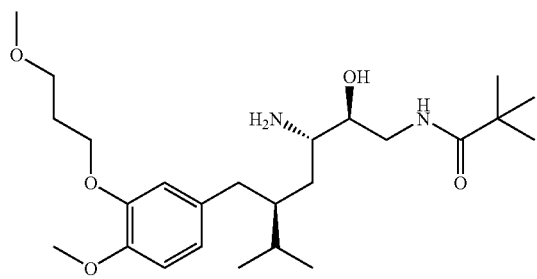

N-{3(S)-Amino-2(S)-hydroxy-5(S)-[4-methoxy-3-(3-methoxypropoxy)benzyl]-6-methylheptyl}-2,2-dimethylpropionamide hydrochloride Analogously to method A 0.010 g of tert-butyl {1(S)-[2-(2,2-dimethylpropionylamino)-1(S)-hydroxyethyl]-3(S)-[4-methoxy-3-(3-methoxypropoxy)benzyl]-4-methylpentyl}carbamate is used to prepare the title compound.

The starting material is prepared as follows:

a) tert-Butyl {1(S)-[2-(2,2-dimethylpropionylamino)-1(S)-hydroxyethyl]-3(S)-[4-methoxy-3-(3-methoxypropoxy)benzyl]-4-methylpentyl}carbamate The stirred solution of 0.025 g of tert-butyl {1(S)-(2-amino-1(S)-hydroxyethyl)-3(S)-[4-methoxy-3-(3-methoxypropoxy)benzyl]-4-methylpentyl}carbamate (Example 36b) and 0.230 ml of ethyl acetate is admixed at 0° C. successively with 0.230 ml of 2M sodium carbonate solution and 0.007 ml of pivaloyl chloride, and stirred at room temperature over another 4 hours. The reaction solution is admixed with water and extracted with ethyl acetate (2×). The combined organic phases are washed successively with water and brine, dried over sodium sulphate and concentrated by evaporation.

The title compound is obtained from the residue by means of flash chromatography (SiO2 60F) as a colourless oil. Rf=0.61 (200:20:1 dichloromethane-methanol-25% conc. ammonia); Rt=5.05 (gradient I).

EXAMPLE 60

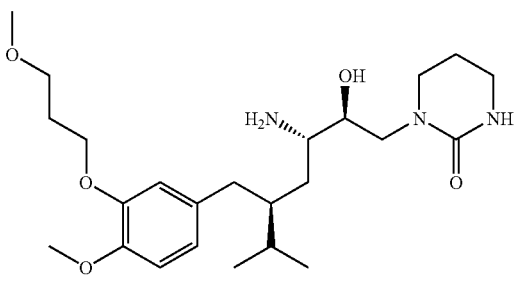

1-{3(S)-Amino-2(S)-hydroxy-5(S)-[4-methoxy-3-(3-methoxypropoxy)benzyl]-6-methylheptyl}tetrahydropyrimidin-2-one hydrochloride Analogously to method A 0.018 g of tert-butyl {1(S)-[1(S)-hydroxy-2-(2-oxotetrahydropyrimidin-1-yl)ethyl]-3(S)-[4-methoxy-3-(3-methoxypropoxy)benzyl]-4-methylpentyl}carbamate is used to prepare the title compound.

The starting material is prepared as follows:

a) tert-Butyl {1(S)-[1(S)-hydroxy-2-(2-oxotetrahydropyrimidin-1-yl)ethyl]-3(S)-[4-methoxy-3-(3-methoxypropoxy)benzyl]-4-methylpentyl}carbamate The solution of 0.035 g of tert-butyl {1(S)-[1(S)-(tert-butyldimethylsilanyloxy)-2-(2-oxotetrahydropyrimidin-1-yl)ethyl]-3(S)-[4-methoxy-3-(3-methoxypropoxy)benzyl]-4-methylpentyl}carbamate in 0.65 ml of tetrahydrofuran is admixed with 0.064 ml of 1M tetrabutylammonium fluoride (in tetrahydrofuran) and stirred at room temperature over 18 hours. The reaction solution is admixed with water and extracted with tert-butyl methyl ether (2×). The combined organic phases are washed with brine, dried over sodium sulphate and concentrated by evaporation. The title compound is obtained from the residue by means of flash chromatography (SiO2 60F) as a colourless oil. Rf=0.36 (200:20:1 dichloromethane-methanol-25% conc. ammonia); Rt=4.44 (gradient I).

b) tert-Butyl {1(S)-[1(S)-(tert-butyldimethylsilanyloxy)-2-(2-oxotetrahydropyrimidin-1-yl)ethyl]-3(S)-3-[4-methoxy-(3-methoxypropoxy)benzyl]-4-methylpentyl}carbamate The stirred solution of 0.042 g of tert-butyl {1(S)-[2-(3-aminopropylamino)-1(S)-hydroxyethyl]-3(S)-[4-methoxy-3-(3-methoxypropoxy)benzyl]-4-methylpentyl}carbamate in 1.2 ml of dichloromethane is cooled to 0° C. and admixed successively with 0.035 g of 2,6-lutidine and 0.054 g of tert-butyldimethylsilyl trifluoromethanesulphonate. The reaction mixture is stirred at 0° C. over 2 hours, poured onto water and extracted with dichloromethane (3×). The combined organic phases are washed with water and dried over sodium sulphate. The filtrate is adjusted to pH 8.0 with imidazole, admixed with 0.013 g of N,N-carbonyldiimidazole and stirred at room temperature over 48 hours. The reaction mixture is concentrated by evaporation and the title compound is obtained from the residue by means of flash chromatography (SiO2 60F) as a yellowish oil. Rf=0.38 (200:20:1 dichloromethane-methanol-25% conc. ammonia).

c) tert-Butyl {1(S)-[2-(3-aminopropylamino)-1(S)-hydroxyethyl]-3(S)-[4-methoxy-3-(3-methoxypropoxy)benzyl]-4-methylpentyl}carbamate A solution of 0.050 g of tert-butyl {3(S)-[4-methoxy-3-(3-methoxypropoxy)benzyl]-4-methyl-1(S)-(R)-oxiranylpentyl}carbamate (Example 1b) in 1.0 ml of isopropanol and 0.071 ml of 1,2-diaminopropane is stirred at 60° C. over 3 hours. The reaction mixture is concentrated by evaporation and the title compound is obtained from the residue by means of flash chromatography (SiO2 60F) as a colourless oil. Rf=0.15 (40:10:1 dichloromethane-methanol-25% conc. ammonia); Rt=3.70 (gradient I).

EXAMPLE 65

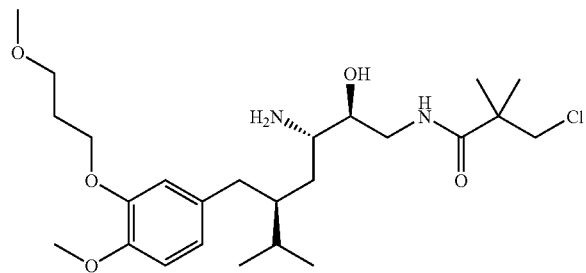

N-{3(S)-Amino-2(S)-hydroxy-5(S)-[4-methoxy-3-(3-methoxypropoxy)benzyl]-6-methylheptyl}-3-chloro-2,2-dimethylpropionamide hydrochloride Analogously to method A, 0.022 g of tert-butyl {1(S)-[2-(3-chloro-2,2-dimethylpropionylamino]-1(S)-hydroxyethyl}-3(S)-[4-methoxy-3-(3-methoxypropoxy)benzyl]-4-methylpentyl}carbamate is used to prepare the title compound.

The starting material is prepared as follows:

a) tert-Butyl {1(S)-[2-(3-chloro-2,2-dimethylpropionylamino]-1(S)-hydroxyethyl}-3(S)-[4-methoxy-3-(3-methoxypropoxy)benzyl]-4-methylpentyl}carbamate A solution of 0.016 g of 3-chloro-2,2-dimethylpropionic acid in 1 ml of dichloromethane is admixed at 0° with 0.020 ml of 1-chloro-N,N-trimethylpropenylamine and the reaction solution is stirred at 0° C. over another 1 hour. The reaction mixture is concentrated by evaporation and the residue is dissolved in 0.5 ml of ethyl acetate. The solution is added to a mixture of 0.025 g tert-butyl {1(S)-(2-acetylamino-1(S)-hydroxyethyl)-3(S)-[4-methoxy-3-(3-methoxypropoxy)benzyl]-4-methylpentyl}carbamate (Example 36b) in 0.5 ml of ethyl acetate and 1 ml of saturated aqueous sodium carbonate solution, and the reaction mixture is stirred at room temperature over 1 hour. The reaction solution is admixed with water and extracted with ethyl acetate (2×). The combined organic phases are washed successively with water and brine, dried over sodium sulphate and concentrated by evaporation. The title compound is obtained from the residue by means of flash chromatography (SiO2 60F) as a yellowish oil. Rf=0.24 (3:2 EtOAc-heptane); Rt=5.14 (gradient I).

According to the processes described in Examples 34, 36, 39, 51, 52, 56, 60 and 65, the following compounds are prepared in an analogous manner:

Examples:
38  N-{3(S)-amino-2(S)-hydroxy-5(S)-[4-methoxy-3-(3-methoxypropoxy)benzyl]-6-methylheptyl}-N-isopropylacetamide hydrochloride
53  N-{3(S)-amino-2(S)-hydroxy-5(S)-[4-methoxy-3-(3-methoxypropoxy)benzyl]-6-methylheptyl}-2-methoxybenzamide hydrochloride
54  1-{3(S)-amino-2(S)-hydroxy-5(S)-[4-methoxy-3-(3-methoxypropoxy)benzyl]-6-methylheptyl}-4(R)-hydroxypyrrolidin-2-one hydrochloride
59  N-{3(S)-amino-2(S)-hydroxy-5(S)-[4-methoxy-3-(3-methoxypropoxy)benzyl]-6-methylheptyl}isobutyramide hydrochloride
61  N-{3(S)-amino-2(S)-hydroxy-5(S)-[4-methoxy-3-(3-methoxypropoxy)benzyl]-6-methylheptyl}adamantine-1-carboxamide hydrochloride
62  N-{3(S)-amino-2(S)-hydroxy-5(S)-[4-methoxy-3-(3-methoxypropoxy)benzyl]-6-methylheptyl}-2,2,N-trimethylpropionamide hydrochloride
63  N-{3(S)-amino-2(S)-hydroxy-5(S)-[4-methoxy-3-(3-methoxypropoxy)benzyl]-6-methylheptyl}-N-ethyl-2,2-dimethylpropionamide hydrochloride
64  N-{3(S)-amino-2(S)-hydroxy-5(S)-[4-methoxy-3-(3-methoxypropoxy)benzyl]-6-methylheptyl}-2-ethylbutyramide hydrochloride
66  N-{3(S)-amino-2(S)-hydroxy-5(S)-[4-methoxy-3-(3-methoxypropoxy)benzyl]-6-methylheptyl}-2-methoxyacetamide hydrochloride
67  3-{3(S)-amino-2(S)-hydroxy-5(S)-[4-methoxy-3-(3-methoxypropoxy)benzyl]-6-methylheptyl}-1,1-dimethylurea hydrochloride
68  N-{3(S)-amino-2(S)-hydroxy-5(S)-[4-methoxy-3-(3-methoxypropoxy)benzyl]-6-methylheptyl}-2-hydroxy-2-methylpropionamide
70  N-{3(S)-amino-2(S)-hydroxy-5(S)-[4-methoxy-3-(3-methoxypropoxy)benzyl]-6-methylheptyl}-1-methylcyclopropanecarboxamide hydrochloride
71  N-{3(S)-amino-2(S)-hydroxy-5(S)-[4-methoxy-3-(3-methoxypropoxy)benzyl]-6-methylheptyl}-1-methylcyclohexanecarboxamide hydrochloride
72  N-{3(S)-amino-2(S)-hydroxy-5(S)-[4-methoxy-3-(3-methoxypropoxy)benzyl]-6-methylheptyl}-2-phenylisobutyramide hydrochloride
73  3-{3(S)-amino-2(S)-hydroxy-5(S)-[4-methoxy-3-(3-methoxypropoxy)benzyl]-6-methylheptyl}-1,1-diethylurea hydrochloride
74  N-{3(S)-amino-2(S)-hydroxy-5(S)-[4-methoxy-3-(3-methoxypropoxy)benzyl]-6-methylheptyl}-2-methoxy-2-methylpropionamide hydrochloride
75  N-{3(S)-amino-2(S)-hydroxy-5(S)-[4-methoxy-3-(3-methoxypropoxy)benzyl]-6-methylheptyl}-2(R)-methoxypropionamide hydrochloride
76  N-{3(S)-amino-2(S)-hydroxy-5(S)-[4-methoxy-3-(3-methoxypropoxy)benzyl]-6-methylheptyl}-2(S)-methoxypropionamide hydrochloride
79  N-{3(S)-amino-2(S)-hydroxy-5(S)-[4-methoxy-3-(3-methoxypropoxy)benzyl]-6-methylheptyl}-2,2-dimethylbutyramide hydrochloride
80  N-{3(S)-amino-2(S)-hydroxy-5(S)-[4-methoxy-3-(3-methoxypropoxy)benzyl]-6-methylheptyl}-2,2-dimethylpentanamide hydrochloride
81  N-{3(S)-amino-2(S)-hydroxy-5(S)-[4-methoxy-3-(3-methoxypropoxy)benzyl]-6-methylheptyl}-2,2-dimethylhexanamide hydrochloride
82  N-{3(S)-amino-2(S)-hydroxy-5(S)-[4-methoxy-3-(3-methoxypropoxy)benzyl]-6-methylheptyl}-1-trifluoromethylcyclobutanecarboxamide hydrochloride 84 2-acetylamino-N-{3(S)-amino-2(S)-hydroxy-5(S)-[4-methoxy-3-(3-methoxypropoxy)benzyl]-6-methylheptyl}-2-methylpropionamide hydrochloride 92 N-{3(S)-amino-2(S)-hydroxy-5(S)-[4-methoxy-3-(3-methoxypropoxy)benzyl]-6-methylheptyl}-2-ethyl-2-methylbutyramide hydrochloride 93 N-{3(S)-amino-2(S)-hydroxy-5(S)-[4-methoxy-3-(3-methoxypropoxy)benzyl]-6-methylheptyl}-2,2-diethylbutyramide hydrochloride 94 N-{3(S)-amino-2(S)-hydroxy-5(S)-[4-methoxy-3-(3-methoxypropoxy)benzyl]-6-methylheptyl}-2-cyclohexylisobutyramide hydrochloride 95 N-{3(S)-amino-2(S)-hydroxy-5(S)-[4-methoxy-3-(3-methoxypropoxy)benzyl]-6-methylheptyl}-2-cyclopentylisobutyramide hydrochloride 96 N-{3(S)-amino-2(S)-hydroxy-5(S)-[4-methoxy-3-(3-methoxypropoxy)benzyl]-6-methylheptyl}-1-phenylcyclopropanecarboxamide hydrochloride 97 N-{3(S)-amino-2(S)-hydroxy-5(S)-[4-methoxy-3-(3-methoxypropoxy)benzyl]-6-methylheptyl}-N-hydroxy-2,2-dimethylpropionamide 98 N-{3(S)-amino-2(S)-hydroxy-5(S)-[4-methoxy-3-(3-methoxypropoxy)benzyl]-6-methylheptyl}-1-phenylcyclobutanecarboxamide hydrochloride 99 N-{3(S)-amino-2(S)-hydroxy-5(S)-[4-methoxy-3-(3-methoxypropoxy)benzyl]-6-methylheptyl}-1-phenylcyclopentanecarboxamide hydrochloride 100 N-{3(S)-amino-2(S)-hydroxy-5(S)-[4-methoxy-3-(3-methoxypropoxy)benzyl]-6-methylheptyl}-2-(3-fluorophenyl)isobutyramide hydrochloride 101 N-{3(S)-amino-2(S-hydroxy-5(S)-[4-methoxy-3-(3-methoxypropoxy)benzyl]-6-methylheptyl}-2-(3-hydroxyphenyl)isobutyramide hydrochloride 102 1-{3(S)-amino-2(S)-hydroxy-5(S)-[4-methoxy-3-(3-methoxypropoxy)benzyl]-6-methylheptyl}-3,3-dimethylpyrrolidin-2-one hydrochloride 103 1-{3(S)-amino-2(S)-hydroxy-5(S)-[4-methoxy-3-(3-methoxypropoxy)benzyl]-6-methylheptyl}-3,3-dimethylpiperidin-2-one hydrochloride 104 1-{3(S)-amino-2(S)-hydroxy-5(S)-[4-methoxy-3-(3-methoxypropoxy)benzyl]-6-methylheptyl}-3,3-dimethylazepan-2-one hydrochloride 105 N-{3(S)-amino-2(S)-hydroxy-5(S)-[4-methoxy-3-(3-methoxypropoxy)benzyl]-6-methylheptyl}-2-(4-chlorophenyl)isobutyramide hydrochloride 106 N-{3(S)-amino-2(S)-hydroxy-5(S)-[4-methoxy-3-(3-methoxypropoxy)benzyl]-6-methylheptyl}-2-(3-chlorophenyl)isobutyramide hydrochloride 107 N-{3(S)-amino-2(S)-hydroxy-5(S)-[4-methoxy-3-(3-methoxypropoxy)benzyl]-6-methylheptyl}-1-cyclohexylcyclobutanecarboxamide hydrochloride 108 N-{3(S)-amino-2(S)-hydroxy-5(S)-[4-methoxy-3-(3-methoxypropoxy)benzyl]-6-methylheptyl}-2-(4-methoxyphenyl)isobutyramide hydrochloride 109 N-{3(S)-amino-2(S)-hydroxy-5(S)-[4-methoxy-3-(3-methoxypropoxy)benzyl]-6-methylheptyl}-2-(3-methoxyphenyl)isobutyramide hydrochloride 110 N-{3(S)-amino-2(S)-hydroxy-5(S)-[4-methoxy-3-(3-methoxypropoxy)benzyl]-6-methylheptyl}-2-p-tolylisobutyramide hydrochloride 111 N-{3(S)-amino-2(S)-hydroxy-5(S)-[4-methoxy-3-(3-methoxypropoxy)benzyl]-6-methylheptyl}-2-m-tolylisobutyramide hydrochloride 112 N-{3(S)-amino-2(S)-hydroxy-5(S)-[4-methoxy-3-(3-methoxypropoxy)benzyl]-6-methylheptyl}-2-(4-fluorophenyl)isobutyramide hydrochloride 113 N-{3(S)-amino-2(S)-hydroxy-5(S)-[4-methoxy-3-(3-methoxypropoxy)benzyl]-6-methylheptyl}-2-piperidin-1-ylisobutyramide dihydrochloride 114 N-{3(S)-amino-2(S)-hydroxy-5(S)-[4-methoxy-3-(3-methoxypropoxy)benzyl]-6-methylheptyl}-2-morpholin-4-ylisobutyramide dihydrochloride 115 N-{3(S)-amino-2(S)-hydroxy-5(S)-[4-methoxy-3-(3-methoxypropoxy)benzyl]-6-methylheptyl}-1-(4-chlorophenyl)cyclobutanecarboxamide hydrochloride 116 N-{3(S)-amino-2(S)-hydroxy-5(S)-[4-methoxy-3-(3-methoxypropoxy)benzyl]-6-methylheptyl}-2-cyclohexyloxy-2-methylpropionamide hydrochloride 117 N-{3-amino-2-hydroxy-5-[4-methoxy-3-(3-methoxypropoxy)benzyl]-6-methylheptyl}-2-(2-fluorophenyl)isobutyramide hydrochloride The starting material is prepared as follows:

a) Methyl 2-(2-fluorophenyl)-2-methylpropionate

In a baked-out round-bottomed flask, 2.60 ml of dicyclohexylamine are dissolved under argon in 15 ml of degassed, anhydrous toluene. The solution is cooled to 0° in an ice bath and 8.20 ml of butyllithium (1.6M solution in hexane) are added dropwise. The mixture is stirred at room temperature over another 15 minutes and subsequently admixed with a solution of 1.28 ml of methyl isobutyrate in 5 ml of toluene. The reaction mixture is stirred over another 15 minutes. In a baked-out Schlenk flask, 0.117 g of bis(dibenzylideneacetone)-palladium and 1.77 g of 1-bromo-2-fluorobenzene are initially charged under argon and the reaction mixture is transferred via cannula into the Schlenk flask. The dark reaction mixture is admixed with 0.060 g of tri-tert-butylphosphonium tetrafluoroborate and stirred at room temperature over 18 hours. The reaction mixture is diluted with 120 ml of dichloromethane, admixed with 20 ml of 1M HCl and filtered through Hyflo. The filtercake is washed with dichloromethane (2×10 ml) and the aqueous phase is removed from the filtrate. The organic phase is washed successively with 1M HCl and brine, dried over sodium sulphate and concentrated by evaporation. The title compound is obtained from the residue by means of flash chromatography (SiO2 60F) as a colourless oil. Rf=0.20 (5:95 EtOAc-heptane); Rt=4.38 (gradient I).

118 N-{3(S)-amino-2(S)-hydroxy-5(S)-[4-methoxy-3-(3-methoxypropoxy)benzyl]-6-methylheptyl}-2-(1H-indol-3-yl)isobutyramide hydrochloride 119 N-{3(S)-amino-2(S)-hydroxy-5(S)-[4-methoxy-3-(3-methoxypropoxy)benzyl]-6-methylheptyl}-2-pyridin-3-ylisobutyramide dihydrochloride 120 N-{3(S)-amino-2(S)-hydroxy-5(S)-[4-methoxy-3-(3-methoxypropoxy)benzyl]-6-methylheptyl}-2-(tetrahydropyran-4-yl)isobutyramide hydrochloride 121 N-{3(S)-amino-2(S)-hydroxy-5(S)-[4-methoxy-3-(3-methoxypropoxy)benzyl]-6-methylheptyl}-2-pyridin-2-ylisobutyramide dihydrochloride 122 N-{3(S)-amino-2(S)-hydroxy-5(S)-[4-methoxy-3-(3-methoxypropoxy)benzyl]-6-methylheptyl}-2-piperidin-4-ylisobutyramide dihydrochloride The starting materials are prepared as follows:

a) tert-Butyl 4-(1-methoxycarbonyl-1-methylethyl)piperidine-1-carboxylate 0.052 g of methyl 2-methyl-2-piperidin-4-ylpropionate hydrochloride are taken up in 2 ml of dioxane and the mixture is admixed with 2 ml of 3M NaOH. The reaction mixture is stirred at room temperature for 30 minutes and 0.079 g of di-tert-butyl dicarbonate is added. The reaction mixture is subsequently stirred at room temperature for 16 hours, adjusted to pH=6 with 2M HCl and extracted with ethyl acetate (2×). The combined organic phases are washed with brine, dried over sodium sulphate and concentrated by evaporation. The title compound is obtained from the residue by means of flash chromatography (SiO2 60F) as a colourless oil. Rf=0.45 (1:2 EtOAc-heptane).

b) Methyl 2-methyl-2-piperidin-4-ylpropionate hydrochloride 0.115 g of methyl 2-methyl-2-pyridin-4-ylpropionate (CAS 79757-27-0) is dissolved in an autoclave in 5 ml of methanol. The solution is admixed with 0.35 ml of 1.2M HCl in methanol and 0.012 g of platinum(IV) oxide, and the reaction mixture is hydrogenated at 4 bar and 23° over 46 hours. The catalyst is filtered off through Hyflo and the filtrate is concentrated by evaporation. The title compound is obtained as a light brown solid. Rf0.05 (200:20:1 dichloromethane-methanol-25% conc. ammonia).

123 2(R)-N-{3(S)-amino-2(S)-hydroxy-5(S)-[4-methoxy-3-(3-methoxypropoxy)benzyl]-6-methylheptyl}-3,3,3-trifluoro-2-methoxy-2-phenylpropionamide hydrochloride

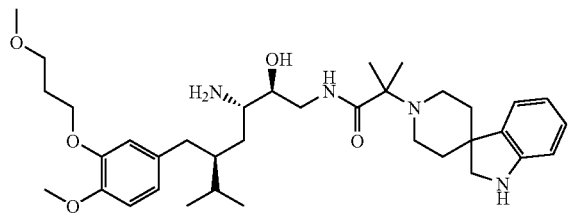

124 N-{3(S)-amino-2(S)-hydroxy-5(S)-[4-methoxy-3-(3-methoxypropoxy)benzyl]-6-methylheptyl}-2-(1,2-dihydrospiro[3H-3,4'-piperidin]-1'-yl)isobutyramide dihydrochloride 125 N-{3(S)-amino-2(S)-hydroxy-5(S)-[4-methoxy-3-(3-methoxypropoxy)benzyl]-6-methylheptyl}-2-(cis-4-hydroxycyclohex-1-yl)isobutyramide hydrochloride The starting materials are prepared as follows:

a) 2-(cis-4-Hydroxy-cyclohexyl)-2-methyl-propionic acid 0.200 g of 2-(cis-4-hydroxy-cyclohexyl)-2-methyl-propionic acid methyl ester are dissolved in 4 ml of methanol. 4 ml of a 1M aqueous lithium hydroxide solution are added and the mixture is stirred for 16 hours at room temperature. The reaction mixture is then neutralised with 1M HCl and concentrated by evaporation. The title compound is identified from the residue by means of flash chromatography (SiO2 60F) based on its Rf value.

b) 2-(cis-4-Hydroxy-cyclohexyl)-2-methyl-propionic acid methyl ester and 2-(trans-4-Hydroxy-cyclohexyl)-2-methyl-propionic acid methyl ester A solution of 2.0 g of 2-(cis/trans-4-hydroxy-cyclohexyl)-2-methyl-propionic acid in 40 ml of methanol is cooled to 0° C. 20 ml of a 2M trimethylsilyldiazomethane solution in hexanes are added dropwise and the reaction solution is left to stand at room temperature for 1 hour. The solution is concentrated under reduced pressure and the residue taken up in ethyl acetate. The solution is washed with saturated aqueous sodium carbonate solution and brine, dried over sodium sulphate and concentrated by evaporation. The residue is purified by flash chromatography (SiO2 60F) to provide the title compounds as colourless oils, the cis isomer eluting first. Rf (cis)=0.11 (1:3 EtOAc-heptane); Rf (trans)=0.09 (1:3 EtOAc-heptane).

c) 2-(cis/trans-4-Hydroxy-cyclohexyl)-2-methyl-propionic acid 2.690 g of 2-(4-hydroxy-phenyl)-2-methyl-propionic acid (29913-51-7) are dissolved in 20 ml of water and 30 ml of 1M NaOH solution. 0.200 g of Raney-Nickel are added and the reaction mixture is hydrogenated at 50 bar and 150° C. for 24 hours. The catalyst is removed by filtration over Hyflo and the filtrate is concentrated by evaporation. The residue is taken up in 200 ml of water and the solution neutralized with 1M HCl to pH 6. The reaction mixture is then extracted with dichloromethane (2×200 ml) and ethyl acetate (2×20 ml) and the combined organic phases are dried over sodium sulphate and concentrated by evaporation to provide the title compounds as a ca. 1:4 mixture of cis/trans-isomers. The white solid is used for the next step without further purification.

126 N-{3(S)-amino-2(S)-hydroxy-5(S)-[4-methoxy-3-(3-methoxypropoxy)benzyl]-6-methylheptyl}-2-(trans-4-hydroxycyclohex-1-yl)isobutyramide hydrochloride 127 N-{3-amino-2-hydroxy-5-[4-methoxy-3-(3-methoxypropoxy)benzyl]-6-methylheptyl}-2-(cis-4-methoxycyclohex-1-yl)isobutyramide hydrochloride The starting materials are prepared as follows:

a) 2-(cis-4-Methoxy-cyclohexyl)-2-methyl-propionic acid 0.200 g of 2-(cis-4-methoxy-cyclohexyl)-2-methyl-propionic acid methyl ester are dissolved in 4 ml of methanol. 4 ml of a 1M aqueous lithium hydroxide solution is added and the mixture is stirred for 16 hours at room temperature. The reaction mixture is then neutralised with 1M HCl and concentrated under reduced pressure. The title compound is identified from the residue by means of flash chromatography (SiO2 60F) based on its Rf value.

b) 2-(cis-4-Methoxy-cyclohexyl)-2-methyl-propionic acid methyl ester 0.500 g of 2-(cis-4-hydroxy-cyclohexyl)-2-methyl-propionic acid methyl ester (Example 125b) are dissolved in 5 ml of dry tetrahydrofuran. 0.120 g of sodium hydride (60% dispersion) is added in portions and the mixture stirred at 40° C. for 1 hour. Methyl iodide (0.233 ml) is added and the mixture heated to 40° C. for 5 hours. The reaction mixture is then cooled to room temperature, quenched with 5 ml of water and extracted with tert-butyl methyl ether (2×50 ml). The combined organic phases are dried over sodium sulphate and concentrated by evaporation. The title compound is identified from the residue by means of flash chromatography (SiO2 60F) based on its Rf value.

128 N-{3-amino-2-hydroxy-5-[4-methoxy-3-(3-methoxypropoxy)benzyl]-6-methylheptyl}-2-(trans-4-methoxycyclohex-1-yl)isobutyramide hydrochloride 129 N-{3(S)-amino-2(S)-hydroxy-5(S)-[4-methoxy-3-(3-methoxypropoxy)benzyl]-6-methylheptyl}-2-cyclohexyl-2(R)-methoxyacetamide hydrochloride The starting material is prepared as follows:

a) (R)-Cyclohexyl-methoxy-acetic acid

An autoclave is charged with a solution of 1.00 g of (R)-α-methoxy-phenyl acetic acid in 20 ml methanol. 0.100 g of Nishimura catalyst are added and the mixture is hydrogenated at 4 bar and 20° C. for 1 hour. The mixture is filtered over Hyflo and the filtrate concentrated by evaporation to provide the title compound as a colourless oil. The crude material is used without further purification. Rf=0.84 (150:54:10:1 dichloromethane-methanol-water-acetic acid).

130 N-{3(S)-amino-2(S)-hydroxy-5(S)-[4-methoxy-3-(3-methoxypropoxy)benzyl]-6-methylheptyl}-2(R)-methoxy-2-phenylacetamide hydrochloride 131 N-{3(S)-amino-2(S)-hydroxy-5(S)-[4-methoxy-3-(3-methoxypropoxy)benzyl]-6-methylheptyl}-2(R)-methoxy-3,3-dimethylbutyramide hydrochloride 132 N-{3(S)-amino-2(S)-hydroxy-5(S)-[4-methoxy-3-(3-methoxypropoxy)benzyl]-6-methylheptyl}-3,3,3-trifluoro-2-methoxy-2-trifluoromethylpropionamide hydrochloride 133 N-{3(S)-amino-2(S)-hydroxy-5(S)-[4-methoxy-3-(3-methoxypropoxy)benzyl]-6-methylheptyl}-3,3,3-trifluoro-2(R)-methoxy-2-methylpropionamide hydrochloride 134 N-{3(S)-amino-2(S)-hydroxy-5(S)-[4-methoxy-3-(3-methoxypropoxy)benzyl]-6-methylheptyl}-3,3,3-trifluoro-2(S)-methoxy-2-methylpropionamide hydrochloride 135 N-{3(S)-amino-2(S)-hydroxy-5(S)-[4-methoxy-3-(3-methoxypropoxy)benzyl]-6-methylheptyl}-2-cyclohexyl-3,3,3-trifluoro-2(R)-methoxypropionamide hydrochloride 136 N-{3(S)-amino-2(S)-hydroxy-5(S)-[4-methoxy-3-(3-methoxypropoxy)benzyl]-6-methylheptyl}-2(R)-methoxy-2-phenylpropionamide hydrochloride 137 N-{3(S)-amino-2(S)-hydroxy-5(S)-[4-methoxy-3-(3-methoxypropoxy)benzyl]-6-methylheptyl}-2-cyclohexyl-2(R)-methoxypropionamide hydrochloride 138 N-{3(S)-amino-2(S)-hydroxy-5(S)-[4-methoxy-3-(3-methoxypropoxy)benzyl]-6-methylheptyl}-1-methoxy-cyclopentanecarboxamide hydrochloride 139 N-{3(S)-amino-2(S)-hydroxy-5(S)-[4-methoxy-3-(3-methoxypropoxy)benzyl]-6-methylheptyl}-1-methoxy-cyclohexanecarboxamide hydrochloride 140 N-{3(S)-Amino-2(S)-hydroxy-5(S)-[4-methoxy-3-(3-methoxy-propoxy)-benzyl]-6-methyl-heptyl}-2(R)-methoxy-3-phenyl-propionamide-hydrochloride 141 N-{3(S)-Amino-2(S)-hydroxy-5(S)-[4-methoxy-3-(3-methoxy-propoxy)-benzyl]-6-methyl-heptyl}-2(R)-methoxy-butyramide-hydrochloride 142 N-{3(S)-Amino-2(S)-hydroxy-5(S)-[4-methoxy-3-(3-methoxy-propoxy)-benzyl]-6-methyl-heptyl}-2-piperidine-3(R,S)-yl-isobutyramide-diacetate The starting materials are prepared according to the processes described in Example 122.

143 N-{3(S)-Amino-2(S)-hydroxy-5(S)-[4-methoxy-3-(3-methoxy-propoxy)-benzyl]-6-methyl-heptyl}-3-cyclohexyl-2(R)-methoxy-propionamide-hydrochloride The starting materials are prepared according to the processes described in Example 129.

144 N-{3(S)-Amino-2(S)-hydroxy-5(S)-[4-methoxy-3-(3-methoxy-propoxy)-benzyl]-6-methyl-heptyl}2-piperidine-2(R,S)-yl-isobutyramide-dihydrochloride 145 N-{3(S)-Amino-2(S)-hydroxy-5(S)-[4-methoxy-3-(3-methoxy-propoxy)-benzyl]-6-methyl-heptyl}-2(R)-methoxy-2-methyl-3-phenyl-propionamide-hydrochloride The starting materials are prepared as follows:

a) (R)-2-Methoxy-2-methyl-3-phenyl-propionic acid 1.69 g of (R)-2-methoxy-2-methyl-3-phenyl-propionic acid methyl ester are dissolved in 40 ml of methanol. 40 ml of a 1M aqueous lithium hydroxide solution are added and the mixture is stirred for 2.5 hours at room temperature. The reaction mixture is neutralised with 1M HCl and concentrated by evaporation. The residue is purified by flash chromatography (SiO2 60F) to provide the title compound as a yellow oil. Rf=0.70 (35:13:5 dichloromethane-methanol-acetic acid).

146 N-{3(S)-Amino-2(S)-hydroxy-5(S)-[4-methoxy-3-(3-methoxy-propoxy)-benzyl]-6-methyl-heptyl}-2(R,S)-(trans-2-hydroxy-cyclohexyl)-isobutyramide-hydrochloride The starting material is prepared as follows:

a) trans-2-[2-tert-Butyl-dimethyl-silanyloxy)-cyclohexyl]-2-methyl-propionic acid Imidazole (0.310 g) is added to a solution of 0.337 g trans-(2-(2-hydroxy-cyclohexyl)-2-methyl propionic acid (34440-72-7) and 0.682 g tert-butyl-dimethyl-chlorosilane in 7 ml of dry N,N-dimethylformamide. The mixture is left to stand at room temperature for 2 hours and is then warmed to 50° for 12 hours. The reaction mixture is poured onto water (30 ml) and the mixture is extracted with tert-butyl methyl ether (2×50 ml). The combined organic phases are washed with saturated aqueous sodium bicarbonate solution (30 ml) and brine (30 ml), dried over sodium sulphate and concentrated under reduced pressure. The residue is taken up in 9 ml of methanol and 3 ml of tetrahydrofuran and the resulting mixture is treated for 1 hour at room temperature with a 10% aqueous potassium carbonate solution (3 ml). The reaction solution is concentrated under reduced pressure to half of the initial volume and the pH is adjusted to 5 with 1M HCl. The mixture is extracted with tert-butyl methyl ether (2×50 ml) and the combined organic phases are washed with brine, dried over sodium sulphate and concentrated under reduced pressure. The residue is purified by means of flash chromatography (SiO2 60F) to provide the title compound as white solid. Rf0.64 (1:2 EtOAc-heptane).

147 N-{3(S)-Amino-2(S)-hydroxy-5(S)-[4-methoxy-3-(3-methoxy-propoxy)-benzyl]-6-methyl-heptyl}-(3(S)-hydroxy-cyclohex-1 (R)-yl)-isobutyramide-hydrochloride The starting materials are prepared as follows:

a) 2-(3(S)-Hydroxy-cyclohex-1(R)-yl)-2-methyl-propionic acid 1.00 g of 2-(cis-3-hydroxy-cyclohexyl)-2-methyl-propionic acid ethyl ester are dissolved in 30 ml of methanol. 30 ml of a 1M aqueous lithium hydroxide solution are added and the mixture is stirred for 16 hours at room temperature. The reaction mixture is neutralised with 1M HCl and concentrated by evaporation. The title compound is identified from the residue by means of flash chromatography (SiO2 60F) based on its Rf value.

b) 2-(3(S)-Hydroxy-cyclohex-1(R)-yl)-2-methyl-propionic acid ethyl ester 3 ml of 1M tetrabutylammonium fluoride solution in tetrahydrofuran are added to a solution of 1.00 g of 2-[3(S)-(tert-butyl-dimethylsilanyloxy)-cyclohex-(1R)-yl]-2-methyl-propionic acid ethyl ester in 3 ml of tetrahydrofuran at 0° C. The reaction is left to stand at room temperature for 1 hour and is then diluted with tert-butyl methyl ether (20 ml) and washed with water (20 ml) and brine (20 ml). The organic layer is dried over sodium sulphate and concentrated by evaporation. The title compound is identified from the residue by means of flash chromatography (SiO2 60F) based on its Rf value.

c) 2-[3(S)-(tert-Butyl-dimethylsilanyloxy)-cyclohex-1(R)-yl]-2-methyl-propionic acid ethyl ester A solution of 21 ml lithium diisopropylamide (ca. 1M in tetrahydrofuran/hexanes) is cooled to −78° b. A solution of 3.72 g [3(S)-(tert-butyl-dimethyl-silanyl-oxy)-cyclohex-1 (R)-yl]-acetic acid ethyl ester (197091-18-2) in 20 ml of tetrahydrofuran is added dropwise over a period of 15 minutes while maintaining the temperature at −78° C. The reaction solution is stirred for 30 minutes at −78° C. and methyl iodide (1.31 ml) is added in one portion. The reaction mixture is warmed to 0° C. over a period of 30 minutes and is then cooled again to −78° C. Lithium diisopropylamide-solution (21 ml) is added dropwise over a period of 15 minutes and the reaction mixture is stirred for 30 minutes at −78° C. 1.31 ml Methyl iodide are added in one portion and the reaction mixture is warmed to room temperature over a period of 16 hours. The reaction mixture is quenched with 0.1M HCl (50 ml) and is then extracted with tert-butyl methyl ether (3×50 ml). The combined organic phases are washed with brine (50 ml), dried over sodium sulphate and concentrated by evaporation. The title compound is identified from the residue by means of flash chromatography (SiO2 60F) based on its Rf value.

148  N-{3(S)-Amino-2(S)-hydroxy-5(S)-[4-methoxy-3-(3-methoxy-propoxy)-benzyl]-6-methyl-heptyl}-2-imidazol-1-yl-isobutyramide-dihydrochloride The starting material is prepared as follows:

a) 2-Imidazol-1-yl-2-methyl-propionic acid 1.54 g of 2-imidazol-1-yl-2-methyl-propionic acid ethyl ester (73828-88-3) are dissolved in 20 ml of methanol. 20 ml of a 3M NaOH are added and the mixture is stirred for 16 hours at 60° C. The reaction mixture is then neutralised with 1M HCl and concentrated by evaporation. The title compound is identified from the residue by means of flash chromatography (SiO2 60F) based on its Rf value.

149  N-{3(S)-Amino-2(S)-hydroxy-5(S)-[4-methoxy-3-(3-methoxy-propoxy)-benzyl]-6-methyl-heptyl}-2-cyano-2,2-dimethyl-acetamide-hydrochloride 150  N-{3(S)-Amino-2(S)-hydroxy-5(S)-[4-methoxy-3-(3-methoxy-propoxy)-benzyl]-6-methyl-heptyl}-2-(1-methylpiperidin-3(R,S)-yl)-isobutyramide-hydrochloride The starting materials are prepared as follows:

a) 2-Methyl-2-(1-methyl-piperidin-3(R,S)-yl)-propionic acid 0.200 g of 2-methyl-2-(1-methyl-piperidin-3(R,S)-yl)-propionic acid methyl ester are dissolved in 4 ml of methanol. 4 ml of a 1M aqueous lithium hydroxide solution are added and the mixture is stirred for 16 hours at room temperature. The reaction mixture is neutralised with 1M HCl and extracted with ethyl acetate (3×50 ml). The organic phases are combined and concentrated by evaporation. The residue is purified by means of flash chromatography (SiO2 60F) to provide the title compound as a colourless oil. Rf 0.15 (150: 54:10:1 dichloromethane-methanol-acetic acid-water).

b) 2-Methyl-2-(1-methyl-piperidin-3(R,S)-yl)-propionic acid methyl ester 0.370 g of 2-methyl-2-piperidin-3(R,S)-yl-propionic acid methyl ester hydrochloride (Example 142) are dissolved in 0.5 ml of 3M NaOH. 2 ml of formic acid and 0.19 ml of formaldehyde (35% aqueous solution) are added and the reaction solution is warmed to 60° C. for 20 hours. The solution is cooled to room temperature, neutralised with 3M NaOH to pH 8-9 and extracted with dichloromethane (3×10 ml). The combined organic phases are washed with water (10 ml), dried over sodium sulphate and concentrated by evaporation. The residue is purified by means of flash chromatography (SiO2 60F) to provide the title compound as a colourless oil. Rf 0.19 (200:20:1 dichloromethane-methanol-25% conc. ammonia).

151  N-{3(S)-Amino-2(S)-hydroxy-5(S)-[4-methoxy-3-(3-methoxy-propoxy)-benzyl]-6-methyl-heptyl}-2-(1-methylpiperidin-2-yl)-isobutyramide-hydrochloride The starting materials are prepared according to the processes described in Example 150.

152  2-(trans-4-Acetylamino-cyclohexyl)-N-{3(S)-amino-2(S)-hydroxy-5(S)-[4-methoxy-3-(3-methoxy-propoxy)-benzyl]-6-methyl-heptyl}-isobutyramide-hydrochloride The starting materials are prepared as follows:

a) trans-2-(4-Acetylamino-cyclohexyl)-2-methyl-propionic acid 0.200 g of trans-2-(4-acetylamino-cyclohexyl)-2-methyl-propionic acid methyl ester are dissolved in 4 ml of methanol. 4 ml of a 1M aqueous lithium hydroxide solution are added and the mixture is stirred for 16 hours at room temperature. The reaction mixture is neutralised with 1M HCl and extracted with ethyl acetate (3×50 ml)—the combined organic phases are concentrated by evaporation. The title compound is identified from the residue by means of flash chromatography (SiO2 60F) based on its Rf value.

b) trans-2-(4-Acetylamino-cyclohexyl)-2-methyl-propionic acid methyl ester

A round bottom flask is charged with 0.422 g of trans-2-(4-azido-cyclohexyl)-2-methyl-propionic acid methyl ester. 0.71 ml of thiocetic acid are added and the solution is stirred for 1 hour at room temperature. After completion of the reaction, the reaction mixture is concentrated by evaporation. The title compound is identified from the residue by means of flash chromatography (SiO2 60F) based on its Rf value.

c) trans-2-(4-Azido-cyclohexyl)-2-methyl-propionic acid methyl ester

Sodium azide (0.761 g) is added to a solution of 0.898 g of cis-2-(4-methanesulfonyloxy-cyclohexyl)-2-methyl-propionic acid methyl ester in 7 ml of N,N-dimethylformamide. The reaction mixture is warmed to 100° C. for 16 hours. The mixture is cooled to room temperature, diluted with 20 ml of water and extracted with tert-butyl methyl ether (3×30 ml). The combined organic phases are washed with brine (20 ml), dried over sodium sulphate and concentrated by evaporation. The title compound is identified from the residue by means of flash chromatography (SiO2 60F) based on its Rf value.

d) cis-2-(4-Methanesulfonyloxy-cyclohexyl)-2-methyl-propionic acid methyl ester

A solution of 1.00 g of 2-(cis-4-hydroxycyclohexyl)-2-methyl-propionic acid methyl ester (Example 125b), 1.38 ml triethylamine and 0.061 g of 4-dimethylaminopyridine in 20 ml of dichloromethane is cooled to 0° C. Methanesulfonylchloride (0.50 ml) is added and the solution is left to stand at room temperature for 16 hours. The solution is poured onto saturated aqueous sodium hydrogen carbonate solution and the phases are separated. The aqueous phase is extracted with dichloromethane (2×50 ml)—the combined organic phases are washed with brine (50 ml), dried over sodium sulphate and concentrated by evaporation. The title compound is identified from the residue by means of flash chromatography (SiO2 60F) based on its Rf value.

153  2-(3(S)-Acetylamino-cyclohex-1(R)-yl)-N-{3(S)-amino-2(S)-hydroxy-5(S)-[4-methoxy-3-(3-methoxy-propoxy)-benzyl]-6-methyl-heptyl}-isobutyramide-hydrochloride The starting materials are prepared according to the processes described in Example 152 starting from 2-(3(S)-hydroxy-cyclohex-1(R)-yl)-2-methyl-propionic acid ethyl ester (Example 147b).

154  N-{3(S)-Amino-2(S)-hydroxy-5(S)-[4-methoxy-3-(3-methoxy-propoxy)-benzyl]-6-methyl-heptyl}-2,2-difluoro-2-phenyl-acetamide-hydrochloride 155  N-{3(S)-Amino-2(S)-hydroxy-5(S)-[4-methoxy-3-(3-methoxy-propoxy)-benzyl]-6-methyl-heptyl}-2-cyclohexyl-2,2-difluoro-acetamide-hydrochloride 156 N-{3(S)-Amino-2(S)-hydroxy-5(S)-[4-methoxy-3-(3-methoxy-propoxy)-benzyl]-6-methyl-heptyl}-2,2-difluoro-2-(tetrahydro-pyran-4-yl)-acetamide

EXAMPLE 50

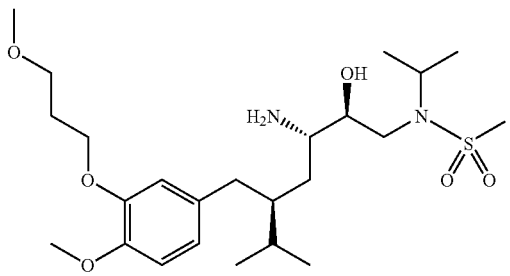

N-{3(S)-Amino-2(S)-hydroxy-5(S)-[4-methoxy-3-(3-methoxypropoxy)benzyl]-6-methylheptyl}-N-isopropylmethanesulphonamide hydrochloride Analogously to method A, 0.046 g of tert-butyl {1(S)-[1(S)-hydroxy-2-(isopropylmethane-sulphonylamino)ethyl]-3(S)-[4-methoxy-3-(3-methoxypropoxy)benzyl]-4-methylpentyl}-carbamate is used to prepare the title compound.

The starting material is prepared as follows:

a) tert-Butyl {1(S)-[1(S)-hydroxy-2-(isopropylmethane-sulphonylamino)ethyl]-3(S)-[4-methoxy-3-(3-methoxypropoxy)benzyl]-4-methylpentyl}carbamate A solution of 0.050 g of tert-butyl {3(S)-[4-methoxy-3-(3-methoxypropoxy)benzyl]-4-methyl-1(S)-(R)-oxiranylpentyl}carbamate (Example 1b) in 1.0 ml of isopropanol and 0.277 ml of isopropylamine is stirred at 60° C. over 3 hours. The reaction mixture is concentrated by evaporation to dryness. The residue is dissolved in 1.5 ml of dichloromethane, admixed successively with 0.018 ml of triethylamine and 0.010 g of methanesulphonyl chloride, and stirred at room temperature over 1 hour. The reaction solution is admixed with water and extracted with tert-butyl methyl ether (2×). The combined organic phases are washed successively with 1M HCl, water and brine, dried over sodium sulphate and concentrated by evaporation. The title compound is obtained from the residue by means of flash chromatography (SiO2 60F) as a slightly yellowish oil. Rf=0.17 (1:1 EtOAc-heptane); Rt=5.16 (gradient I).

According to the processes described in Example 50, the following compounds are prepared in an analogous manner:

Examples:
69 N-{3(S)-amino-2(S)-hydroxy-5(S)-[4-methoxy-3-(3-methoxypropoxy)benzyl]-6-methylheptyl}methanesulphonamide hydrochloride
83 N-{3(S)-amino-2(S)-hydroxy-5(S)-[4-methoxy-3-(3-methoxypropoxy)benzyl]-6-methylheptyl}benzenesulphonamide hydrochloride
85 N-{3(S)-amino-2(S)-hydroxy-5(S)-[4-methoxy-3-(3-methoxypropoxy)benzyl]-6-methylheptyl}thiophene-2-sulphonamide hydrochloride
86 N-{3(S)-amino-2(S)-hydroxy-5(S)-[4-methoxy-3-(3-methoxypropoxy)benzyl]-6-methylheptyl}-C-phenyl-methanesulphonamide hydrochloride
87 N-{3(S)-amino-2(S)-hydroxy-5(S)-[4-methoxy-3-(3-methoxypropoxy)benzyl]-6-methylheptyl}propane-1-sulphonamide hydrochloride
88 N-{3(S)-amino-2(S)-hydroxy-5(S)-[4-methoxy-3-(3-methoxypropoxy)benzyl]-6-methylheptyl}butane-1-sulphonamide hydrochloride
89 N-{3(S)-amino-2(S)-hydroxy-5(S)-[4-methoxy-3-(3-methoxypropoxy)benzyl]-6-methylheptyl}propane-2-sulphonamide hydrochloride
90 N-{3(S)-amino-2(S)-hydroxy-5(S)-[4-methoxy-3-(3-methoxypropoxy)benzyl]-6-methylheptyl}cyclopropanesulphonamide hydrochloride
91 N-{3(S)-amino-2(S)-hydroxy-5(S)-[4-methoxy-3-(3-methoxypropoxy)benzyl]-6-methylheptyl}ethanesulphonamide hydrochloride
157 2-Methyl-propane-2-sulfonic acid {3(S)-amino-2(S)-hydroxy-5(S)-[4-methoxy-3-(3-methoxy-propoxy)-benzyl]-6-methyl-heptyl}-amide hydrochloride
158 2-Cyclohexyl-propane-2-sulfonic acid {3(S)-amino-2(S)-hydroxy-5(S)-[4-methoxy-3-(3-methoxy-propoxy)-benzyl]-6-methyl-heptyl}amide hydrochloride The starting materials are prepared as follows:

a) 2-Cyclohexyl-propane-2-sulfonyl chloride 2 mmol of phosphoroxytrichloride are added to a solution of 1 mmol of 2-cyclohexyl-propane-2-sulfonic acid in acetonitrile and the reaction mixture is heated to reflux for 2 hours. The reaction mixture is cooled to room temperature, carefully quenched by the addition of water and extracted with tert-butyl methyl ether. The organic phase is dried over sodium sulphate and concentrated by evaporation. The crude title compound is used without further purification.

b) 2-Cyclohexyl-propane-2-sulfonic acid 10 ml of an aqueous hydrogen peroxide solution (30% wt) are added to a stirred solution of 1 mmol of 2-cyclohexyl-propane-2-thiol in acetic and the mixture is then heated at 60° C. overnight. The reaction mixture is cooled to room temperature and the solvent removed under reduced pressure. The crude title compound is used without further purification.

c) 2-Cyclohexyl-propane-2-thiol 1 mmol of thiourea is added to a stirred solution of 1 mmol of (1-bromo-1-methyl-ethyl)-cyclohexane [BRN 2424910] in methanol and the mixture is stirred for 12 hours at room temperature. The solvent is removed under reduced pressure and the residue is then suspended in 10 ml of 2N NaOH and heated at 60° C. for 3 hours. The reaction mixture is cooled to room temperature and extracted with tert-butyl methyl ether (3×). The combined organic phases are dried over sodium sulphate and concentrated by evaporation. The crude title compound is used without further purification.

| No. | Appearance | $R_f$ (system) | Rt (method) |
|---|---|---|---|
| 1 | white powder | 0.13 (A) | 11.43 (II) |
| 2 | white foam | 0.20 (A) | 3.47 (I) |
| 3 | white powder | 0.16 (A) | 3.21 (I) |
| 4 | beige powder | 0.06 (A) | 2.88 (I) |
| 5 | beige powder | 0.06 (A) | 2.88 (I) |
| 6 | beige powder | 0.04 (A) | 2.90 (I) |
| 7 | beige powder | 0.03 (A) | 2.90 (I) |
| 8 | beige powder | 0.19 (A) | 2.95 (I) |
| 9 | beige powder | 0.12 (A) | 3.17 (I) |
| 10 | white foam | 0.28 (A) | 3.64 (I) |
| 11 | white solid | 0.10 (A) | 3.13 (I) |
| 12 | white solid | 0.03 (A) | 3.11 (I) |
| 13 | white solid | 0.08 (A) | 3.17 (I) |
| 14 | white solid | 0.20 (A) | 3.18 (I) |
| 15 | white solid | 0.11 (A) | 3.02 (I) |
| 16 | white solid | 0.12 (A) | 3.03 (I) |
| 17 | yellow solid | 0.11 (A) | 2.82 (I) |

-continued

| No. | Appearance | $R_f$(system) | Rt (method) |
|---|---|---|---|
| 18 | yellow solid | 0.14 (A) | 3.04 (I) |
| 19 | yellow solid | 0.05 (A) | 2.86 (I) |
| 20 | yellow solid | 0.14 (A) | 3.18 (I) |
| 21 | yellow solid | 0.26 (A) | 3.21 (I) |
| 22 | yellow solid | 0.06 (A) | 2.90 (I) |
| 23 | white solid | 0.09 (A) | 3.00 (I) |
| 24 | white solid | 0.26 (A) | 2.98 (I) |
| 25 | white solid | 0.05 (A) | 2.93 (I) |
| 26 | white solid | 0.20 (A) | 3.02 (I) |
| 27 | white solid | 0.09 (A) | 3.08 (I) |
| 28 | white solid | 0.14 (A) | 3.16 (I) |
| 29 | white solid | 0.08 (A) | 2.98 (I) |
| 30 | white solid | 0.16 (A) | 2.96 (I) |
| 31 | white solid | 0.22 (A) | 3.15 (I) |
| 32 | white solid | 0.59 (A) | 3.36 (I) |
| 33 | white solid | 0.16 (A) | 3.01 (I) |
| 34 | white powder | 0.27 (A) | 3.31 (I) |
| 35 | white solid | 0.20 (A) | 3.07 (I) |
| 36 | white powder | 0.11 (A) | 3.14 (I) |
| 37 | yellowish oil | 0.88 (A) | 4.14 (I) |
| 38 | white solid | 0.22 (A) | 3.76 (I) |
| 39 | white solid | 0.22 (A) | 3.46 (I) |
| 40 | white powder | 0.14 (A) | 3.23 (I) |
| 41 | white solid | 0.17 (A) | 3.15 (I) |
| 42 | white solid | 0.15 (A) | 3.15 (I) |
| 43 | white solid | 0.20 (A) | 3.53 (I) |
| 44 | white solid | 0.16 (A) | 3.52 (I) |
| 45 | white solid | 0.13 (A) | 3.73 (I) |
| 46 | white solid | 0.24 (A) | 3.15 (I) |
| 47 | white solid | 0.22 (A) | 3.18 (I) |
| 48 | white solid | 0.17 (A) | 3.73 (I) |
| 49 | white solid | 0.21 (A) | 3.42 (I) |
| 50 | white solid | 0.97 (A) | 3.59 (I) |
| 51 | white solid | 0.24 (A) | 3.40 (I) |
| 52 | white solid | 0.33 (A) | 3.73 (I) |
| 53 | white solid | 0.32 (A) | 3.85 (I) |
| 54 | white solid | 0.13 (A) | 3.05 (I) |
| 55 | white solid | 0.07 (A) | 3.06 (I) |
| 56 | white solid | 0.21 (A) | 3.75 (I) |
| 57 | white solid | 0.06 (A) | 2.86 (I) |
| 58 | white solid | 0.22 (A) | 2.86 (I) |
| 59 | yellowish oil | 0.20 (B) | 3.51 (I) |
| 60 | white solid | 0.12 (A) | 3.75 (I) |
| 61 | white solid | 0.31 (A) | 4.34 (I) |
| 62 | white solid | 0.15 (A) | 3.44 (I) |
| 63 | white solid | 0.22 (A) | 3.52 (I) |
| 64 | white solid | 0.69 (A) | 3.87 (I) |
| 65 | white solid | 0.24 (A) | 3.72 (I) |
| 66 | white solid | 0.27 (A) | 3.33 (I) |
| 67 | white solid | 0.25 (A) | 3.28 (I) |
| 68 | yellow oil | 0.12 (A) | 3.23 (I) |
| 69 | white solid | 0.12 (A) | 3.30 (I) |
| 70 | white solid | 0.33 (A) | 3.64 (I) |
| 71 | white solid | 0.32 (A) | 4.18 (I) |
| 72 | white solid | 0.45 (A) | 4.15 (I) |
| 73 | white solid | 0.29 (A) | 3.63 (I) |
| 74 | white solid | 0.29 (A) | 3.47 (I) |
| 75 | white solid | 0.30 (A) | 3.38 (I) |
| 76 | white solid | 0.30 (A) | 3.39 (I) |
| 77 | white solid | 0.09 (A) | 3.27 (I) |
| 78 | white solid | 0.12 (A) | 3.40 (I) |
| 79 | white solid | 0.76 (A) | 3.90 (I) |
| 80 | white solid | 0.76 (A) | 4.15 (I) |
| 81 | white solid | 0.76 (A) | 4.39 (I) |
| 82 | white solid | 0.76 (A) | 3.96 (I) |
| 83 | white solid | 0.61 (A) | 3.84 (I) |
| 84 | white solid | 0.60 (B) | 3.17 (I) |
| 85 | yellowish oil | 0.52 (A) | 3.77 (I) |
| 86 | yellowish oil | 0.52 (A) | 3.84 (I) |
| 87 | yellowish oil | 0.49 (A) | 3.52 (I) |
| 88 | yellowish oil | 0.51 (A) | 3.74 (I) |
| 89 | yellowish oil | 0.33 (A) | 3.52 (I) |
| 90 | yellowish oil | 0.39 (A) | 3.48 (I) |
| 91 | yellowish oil | 0.41 (A) | 3.36 (I) |
| 92 | white solid | 0.43 (A) | 4.08 (I) |
| 93 | yellowish oil | 0.36 (A) | 4.28 (I) |
| 94 | white solid | 0.55 (A) | 4.49 (I) |
| 95 | white solid | 0.28 (A) | 4.27 (I) |
| 96 | beige solid | 0.10 (C) | 4.03 (I) |
| 97 | white oil | 0.38 (A) | 3.84 (I) |
| 98 | beige solid | 0.10 (C) | 4.13 (I) |
| 99 | beige solid | 0.09 (C) | 4.32 (I) |
| 100 | white solid | 0.44 (C) | 4.12 (I) |
| 101 | white solid | 0.29 (A) | 3.64 (I) |
| 102 | white solid | 0.05 (C) | 3.60 (I) |
| 103 | white solid | 0.04 (C) | 3.85 (I) |
| 104 | white solid | 0.05 (C) | 4.01 (I) |
| 105 | white solid | 0.37 (A) | 4.32 (I) |
| 106 | white solid | 0.35 (A) | 4.31 (I) |
| 107 | white solid | 0.33 (A) | 4.47 (I) |
| 108 | white solid | 0.11 (A) | 4.04 (I) |
| 109 | white solid | 0.12 (A) | 4.07 (I) |
| 110 | white solid | 0.42 (A) | 4.25 (I) |
| 111 | white solid | 0.39 (A) | 4.25 (I) |
| 112 | white solid | 0.25 (A) | 4.18 (I) |
| 113 | white solid | 0.41 (A) | 3.18 (I) |
| 114 | white solid | 0.26 (A) | 3.03 (I) |
| 115 | white solid | 0.31 (A) | 4.38 (I) |
| 116 | white solid | 0.50 (A) | 4.44 (I) |
| 117 | white solid | 0.21 (A) | 4.04 (I) |
| 118 | white solid | 0.26 (A) | 4.00 (I) |
| 119 | white solid | 0.21 (A) | 2.97 (I) |
| 120 | white solid | 0.30 (A) | 3.54 (I) |
| 121 | white solid | 0.19 (A) | 3.05 (I) |
| 122 | white solid | 0.15 (E) | 2.97 (I) |
| 123 | white solid | 0.33 (A) | 4.26 (I) |
| 129 | white solid | 0.24 (A) | 4.15 (I) |
| 130 | white solid | 0.33 (A) | 3.83 (I) |
| 136 | white solid | 0.07 (C) | 4.03 (I) |
| 140 | white solid | 0.35 (A) | 3.93 (I) |
| 141 | white solid | 0.28 (A) | 3.48 (I) |
| 142 | white solid | 0.11 (E) | 3.03 (I) |
| 143 | white solid | 0.07 (C) | 4.39 (I) |
| 144 | white solid | 0.13 (D) | 3.07 (I) |
| 145 | white solid | 0.07 (C) | 4.05 (I) |

Tin-layer chromatography eluent systems:
A dichloromethane-methanol-25% conc. ammonia = 200:20:1
B dichloromethane-methanol-25% conc. ammonia = 40:10:1
C dichloromethane-methanol-25% conc. ammonia = 200:10:1
D dichloromethane-methanol-25% conc. ammonia = 200:40:1
E dichloromethane-methanol-water-conc. acetic acid = 150:54:10:1

Thin-layer chromatography eluent systems:

A dichloromethane-methanol-25% conc. ammonia=200:20:1

B dichloromethane-methanol-25% conc. ammonia=40:10:1

C dichloromethane-methanol-25% conc. ammonia=200:10:1

D dichloromethane-methanol-25% conc. ammonia=200:40:1

E dichloromethane-methanol-water-conc. acetic acid=150:54:10:1

The invention claimed is:

1. A compound of the formula

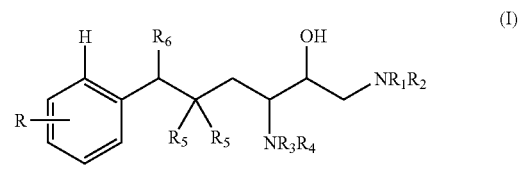

(I)

wherein:

$R_1$ is
- a) hydrogen, hydroxyl or amino; or
- b) $C_1$-$C_8$-alkyl, $C_3$-$C_8$-cycloalkyl, $C_1$-$C_8$-alkanoyl, $C_1$-$C_8$-alkoxycarbonyl, aryl-$C_0$-$C_4$-alkyl or heterocyclyl-$C_0$-$C_4$-alkyl, which radicals may be substituted by 1-4 $C_1$-$C_8$-alkyl, halogen, oxo, cyano, trifluoromethyl, $C_1$-$C_8$-alkoxy, $C_1$-$C_8$-alkoxycarbonyl, aryl or heterocyclyl;

$R_2$ is
- a) $C_1$-$C_8$-alkyl, $C_3$-$C_8$-cycloalkyl, $C_1$-$C_8$-alkylsulphonyl, $C_3$-$C_8$-cycloalkylsulphonyl, aryl-$C_0$-$C_8$-alkylsulphonyl, heterocyclylsulphonyl, $C_3$-$C_{12}$-cycloalkyl-$C_1$-$C_8$-alkanoyl, aryl-$C_1$-$C_8$-alkanoyl, aryl-$C_3$-$C_8$-cycloalkanoyl, $C_1$-$C_8$-alkanoyl, $C_1$-$C_8$-alkoxycarbonyl, optionally N-mono- or N,N-di-$C_1$-$C_8$-alkylated carbamoyl-$C_0$-$C_8$-alkyl, aryl-$C_0$-$C_4$-alkyl or heterocyclyl-$C_0$-$C_4$-alkyl, which radicals may be substituted by 1-4 $C_1$-$C_8$-alkyl, $C_3$-$C_8$-cycloalkyl, $C_3$-$C_8$-cycloalkoxy, amino, $C_{1-6}$-alkylamino, di-$C_{1-6}$-alkylamino, $C_1$-$C_6$-alkanoylamino, $C_1$-$C_8$-alkoxycarbonylamino, halogen, oxo, cyano, hydroxyl, trifluoromethyl, $C_1$-$C_8$-alkoxy, $C_1$-$C_8$-alkoxycarbonyl, aryl or heterocyclyl; or
- b) together with $R_1$ and the nitrogen atom to which they are bonded is a saturated or partly unsaturated, 4-8-membered, heterocyclic ring which may contain an additional nitrogen, oxygen or sulphur atom or an —SO— or —SO2— group, and the additional nitrogen atom may optionally be substituted by $C_1$-$C_8$-alkyl, $C_1$-$C_8$-alkanoyl, $C_1$-$C_8$-alkoxycarbonyl, aryl or heteroaryl radicals, in which case this heterocyclic ring may be part of a bicyclic or tricyclic ring system having a total of up to 16 members and the second ring may also contain a nitrogen, oxygen or sulphur atom or an —SO— or —SO2— group, and the nitrogen atom of the second ring may optionally be substituted by $C_1$-$C_8$-alkyl, $C_1$-$C_8$-alkanoyl, $C_1$-$C_8$-alkoxycarbonyl, aryl or heterocyclyl radicals, and all ring systems mentioned may be substituted by 1-4 $C_1$-$C_8$-alkyl, halogen, hydroxyl, oxo, trifluoromethyl, $C_1$-$C_8$-alkoxy, $C_1$-$C_8$-alkoxy-$C_1$-$C_8$-alkyl, $C_1$-$C_8$-alkoxy-$C_1$-$C_8$-alkoxy, $C_1$-$C_8$-alkoxycarbonylamino, $C_1$-$C_8$-alkanoylamino, $C_1$-$C_8$-alkylamino, N,N-di-$C_1$-$C_8$-alkylamino, aryl-$C_0$-$C_4$-alkyl, aryloxy-$C_0$-$C_4$-alkyl, aryl-$C_0$-$C_4$-alkyl-$C_1$-$C_8$-alkoxy, aryloxy-$C_0$-$C_4$-alkyl-$C_1$-$C_8$-alkoxy, heterocyclyl-$C_0$-$C_4$-alkyl, heterocyclyloxy-$C_0$-$C_4$-alkyl, heteroaryl-$C_0$-$C_4$-alkyl-$C_1$-$C_8$-alkoxy or heterocyclyloxy-$C_0$-$C_4$-alkyl-$C_1$-$C_8$-alkoxy;

$R_3$ is hydrogen, $C_1$-$C_4$-alkyl, $C_1$-$C_8$-alkoxycarbonyl or $C_1$-$C_8$-alkanoyl;

$R_4$ is hydrogen, $C_1$-$C_4$-alkyl, $C_1$-$C_8$-alkoxycarbonyl or $C_1$-$C_8$-alkanoyl;

$R_5$ is in each case independently hydrogen, $C_1$-$C_8$-alkyl, or, together with the carbon atom to which they are bonded, are a $C_3$-$C_8$-cycloalkylidene radical;

$R_6$ is hydrogen or hydroxyl;

R, in each case independently, are 1-4 radicals selected from:

hydrogen, halogen, $C_1$-$C_8$-alkyl, 3- to 8-membered cycloalkyl, polyhalo-$C_1$-$C_4$-alkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, 3- to 8-membered cycloalkoxy-$C_1$-$C_4$-alkyl, hydroxyl, $C_1$-$C_8$-alkanoyloxy-$C_1$-$C_4$-alkyl, hydroxy-$C_2$-$C_8$-alkyl, $C_1$-$C_4$-alkylthio-$C_1$-$C_4$-alkyl, $C_1$-$C_4$-alkylsulphonyl-$C_1$-$C_4$-alkyl, thiazolylthio-$C_1$-$C_4$-alkyl, thiazolinylthio-$C_1$-$C_4$-alkyl, imidazolylthio-$C_1$-$C_4$-alkyl, optionally N-oxidized pyridylthio-$C_1$-$C_4$-alkyl, pyrimidinylthio-$C_1$-$C_4$-alkyl, optionally partially hydrogenated pyridyl- or N-oxidopyridyl-$C_1$-$C_4$-alkyl, $C_1$-$C_4$-alkylsulphonylamino-$C_1$-$C_4$-alkyl, trifluoro-$C_1$-$C_8$-alkylsulphonylamino-$C_1$-$C_4$-alkyl, pyrrolidino-$C_1$-$C_4$-alkyl, piperidino-$C_1$-$C_4$-alkyl, piperazino-$C_1$-$C_4$-alkyl, N'-$C_1$-$C_4$-alkylpiperazino-$C_1$-$C_4$-alkyl, N'-$C_2$-$C_8$-alkanoylpiperazino-$C_1$-$C_4$-alkyl, morpholino-$C_1$-$C_4$-alkyl, thiomorpholino-$C_1$-$C_4$-alkyl, S-oxothiomorpholino-$C_1$-$C_4$-alkyl, S,S-dioxothiomorpholino-$C_1$-$C_4$-alkyl, cyano-$C_1$-$C_4$-alkyl, carboxy-$C_1$-$C_4$-alkyl, $C_1$-$C_4$-alkoxycarbonyl-$C_1$-$C_4$-alkyl, carbamoyl-$C_1$-$C_8$-alkyl, N-mono- or N,N-di-$C_1$-$C_4$-alkylcarbamoyl-$C_1$-$C_4$-alkyl, unsubstituted or mono-, di- or tri-$C_1$-$C_4$-alkyl-, —$C_1$-$C_4$-alkoxy-, -hydroxy-, —$C_1$-$C_4$-alkylamino-, -di-$C_1$-$C_4$-alkylamino-, -halogen- or -trifluoromethyl-substituted phenyl or naphthyl, hydroxy-$C_2$-$C_8$-alkoxy, halo-$C_2$-$C_8$-(hydroxy)alkoxy, $C_1$-$C_8$-alkylsulphonyl-$C_1$-$C_4$-(hydroxy)alkoxy, amino-$C_1$-$C_4$-alkyl, $C_1$-$C_4$-alkylamino-$C_1$-$C_4$-alkyl, N,N-di-$C_1$-$C_4$-alkylamino-$C_1$-$C_4$-alkyl, N—$C_1$-$C_4$-alkanoylamino-$C_1$-$C_4$-alkyl, $C_1$-$C_4$-alkoxycarbonylamino-$C_1$-$C_4$-alkyl, optionally partially hydrogenated pyridyl- or N-oxidopyridyl-$C_1$-$C_4$-alkyl, piperazino-$C_1$-$C_4$-alkyl, N'-$C_1$-$C_4$-alkylpiperazino-$C_1$-$C_4$-alkyl, N'-$C_2$-$C_8$-alkanoylpiperazino-$C_1$-$C_4$-alkyl, morpholino-$C_1$-$C_4$-alkyl, thiomorpholino-$C_1$-$C_4$-alkyl, S-oxothiomorpholino-$C_1$-$C_4$-alkyl, S,S-dioxothiomorpholino-$C_1$-$C_4$-alkyl, amino-$C_1$-$C_4$-alkoxy, $C_1$-$C_4$-alkylamino-$C_1$-$C_4$-alkoxy, N,N-di-$C_1$-$C_4$-alkylamino-$C_1$-$C_4$-alkoxy, $C_1$-$C_4$-alkanoyl-amino-$C_1$-$C_4$-alkoxy, $C_1$-$C_8$-alkoxycarbonylamino-$C_1$-$C_4$-alkoxy, $C_1$-$C_8$-alkanoyl-$C_2$-$C_4$-alkoxy which bears the alkanoyl group in a position higher than the α-position, $C_1$-$C_8$-alkoxy, 3- to 8-membered cycloalkoxy, $C_2$-$C_8$-alkenyloxy, 3- to 8-membered cycloalkoxy-$C_1$-$C_4$-alkoxy, $C_1$-$C_8$-alkoxy-$C_1$-$C_8$-alkoxy, $C_1$-$C_4$-alkoxy-$C_2$-$C_4$-alkenyl, $C_2$-$C_8$-alkenyloxy-$C_1$-$C_4$-alkoxy, $C_1$-$C_4$-alkoxy-$C_2$-$C_4$-alkenyloxy, $C_2$-$C_8$-alkenyloxy-$C_1$-$C_4$-alkyl, $C_1$-$C_4$-alkylthio-$C_1$-$C_4$-alkoxy, $C_1$-$C_8$-alkylsulphonyl-$C_1$-$C_4$-alkoxy, $C_1$-$C_4$-alkylthio-$C_1$-$C_4$-(hydroxy)alkoxy, unsubstituted or mono-, di- or tri-$C_1$-$C_4$-alkyl-, —$C_1$-$C_4$-alkoxy-, -hydroxy-, —$C_1$-$C_4$-alkylamino-, -di-$C_1$-$C_4$-alkylamino-, -halo- and/or -trifluoromethyl-substituted phenyl- or naphthyl-$C_1$-$C_4$-alkoxy, polyhalo-$C_1$-$C_4$-alkoxy, optionally partially hydrogenated pyridyl- or N-oxidopyridyl-$C_1$-$C_4$-alkoxy, thiazolyl-$C_1$-$C_4$-alkoxy, optionally N-oxidized morpholino-$C_1$-$C_4$-alkoxy, thiazolylthio-$C_1$-$C_4$-alkoxy, thiazolinylthio-$C_1$-$C_4$-alkoxy, imidazolylthio-$C_1$-$C_4$-alkoxy, optionally N-oxidized pyridylthio-$C_1$-$C_4$-alkoxy, pyrimidinylthio-$C_1$-$C_4$-alkoxy, amino-$C_1$-$C_4$-alkoxy, $C_1$-$C_4$-alkylamino-$C_1$-$C_4$-alkoxy, N,N-di-$C_1$-$C_4$-alkylamino-$C_1$-$C_4$-alkoxy, $C_1$-$C_8$-alkanoylamino-$C_1$-$C_4$-alkoxy, $C_1$-$C_8$-alkylsulphonylamino-$C_1$-$C_4$-alkoxy, trifluoro-$C_1$-$C_8$-alkylsulphonyl-$C_1$-$C_4$-alkoxy, pyrrolidino-$C_1$-$C_4$-alkoxy, piperidino-$C_1$-$C_4$-alkoxy, cyano-$C_1$-$C_4$-alkoxy, carboxy-$C_1$-$C_4$-alkoxy, $C_1$-$C_4$-alkoxycarbonyl-$C_1$-$C_4$-alkoxy, carbamoyl-$C_1$-$C_4$-alkoxy, N—$C_1$-$C_8$-alkylcarbamoyl-$C_1$-$C_4$-alkoxy or N-mono- or N,N-di-$C_1$-$C_4$-alkylcarbamoyl-$C_1$-$C_4$-alkoxy, carboxy-$C_1$-$C_4$-alkyl, $C_1$-$C_4$-alkoxycarbonyl-$C_1$-$C_4$-alkyl, carbamoyl-$C_1$-$C_8$-alkyl, N-mono- or N,N-di-$C_1$-$C_4$-alkylcarbamoyl-$C_1$-$C_4$-alkyl, carboxy-$C_1$-$C_4$-alkoxy, $C_1$-$C_4$-alkoxycarbonyl-$C_1$-$C_4$-alkoxy, carbamoyl-$C_1$-$C_8$-alkoxy, N-Mono- or N,N-di-$C_1$-$C_4$-alkylcarbamoyl-$C_1$-$C_4$-alkoxy, $C_1$-$C_4$-alkylamino or N,N-di-$C_1$-$C_4$-alkylamino, or salt or prodrug thereof, or where one or more atoms are replaced by their stable, non-radioactive isotopes, preferably pharmaceutically usable salt thereof.

2. The compound according to claim 1, wherein:

$R_1$ is a) hydrogen; or
   b) $C_1$-$C_8$-alkyl or $C_3$-$C_8$-cycloalkyl;

$R_2$ is a) $C_1$-$C_8$-alkyl, $C_3$-$C_8$-cycloalkyl, $C_1$-$C_8$-alkanoyl, heterocyclyl-$C_1$-$C_8$-alkanoyl, $C_3$-$C_{12}$-cycloalkyl-$C_1$-$C_8$-alkanoyl or aryl-$C_1$-$C_8$-alkanoyl, which radicals may be substituted by 1-4 $C_1$-$C_8$-alkyl, $C_{1-6}$-alkylamino, cyano, halogen, hydroxyl, $C_1$-$C_6$-alkanoylamino, $C_1$-$C_8$-alkoxy, oxo, trifluoromethyl or aryl; or
   b) together with $R_1$ and the nitrogen atom to which they are bonded are a saturated or partly unsaturated, 4-8-membered, heterocyclic ring which may contain an additional nitrogen or oxygen atom, in which case the additional nitrogen atom may optionally be substituted by $C_1$-$C_8$-alkyl or $C_1$-$C_8$-alkanoyl, and this heterocyclic ring may be part of a bicyclic or tricyclic ring system having a total of up to 16 ring members and the second ring may also contain a nitrogen or oxygen atom, in which case the nitrogen atom of the second ring may optionally be substituted by $C_1$-$C_8$-alkyl or $C_1$-$C_8$-alkanoyl, and all ring systems mentioned may be substituted by 1-4 $C_1$-$C_8$-alkyl, hydroxyl, oxo, $C_1$-$C_8$-alkoxy, $C_1$-$C_8$-alkoxy-$C_1$-$C_8$-alkoxy, $C_1$-$C_8$-alkanoylamino or aryloxy-$C_0$-$C_4$-alkyl-$C_1$-$C_8$-alkoxy;

$R_3$ is hydrogen;
$R_4$ is hydrogen;
$R_5$ are each independently hydrogen or $C_1$-$C_8$-alkyl;
$R_6$ is hydrogen;
R are each independently 1-4 radicals selected from: hydrogen, $C_1$-$C_8$-alkyl, halogen, trifluoromethyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_8$-alkoxy, $C_1$-$C_4$-alkoxy-$C_1$-$C_4$-alkoxy, or pharmaceutically usable salt thereof.

3. The compound according to claim 1 of the formula

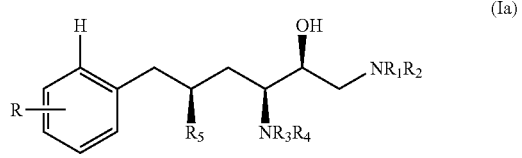

(Ia)

wherein R, $R_1$, $R_2$, $R_3$, $R_4$ and $R_5$ are each as defined in claim 1.

4. The compound according to claim 1, wherein $R_2$ together with $R_1$ and the nitrogen atom to which they are bonded is a substituted or unsubstituted hetero cyclic ring selected from the group consisting of pyrrolidino, piperidino, pyridinyl, piperazino, morpholino, thiomorpholino, furanyl, tetrahydrofuranyl, pyranyl, tetrahydropyranyl, thiazolyl, oxazolyl, imidazolyl, indolinyl, isoindolinyl, 2,3-dihydrobenzimidazolyl, 1,2,3,4-tetrahydroquinolyl, 1,2,3,4-tetrahydroisoquinolyl, 1,2,3,4-tetrahydro-1,3-benzodiazinyl, 1,2,3,4-tetrahydro-1,4-benzodiazinyl, 3,4-dihydro-2H-1,4-benzoxazinyl, 3,4-dihydro-2H-1,4-benzothiazinyl, 3,4-dihydro-2H-1,3-benzothiazinyl, 3,4,5,6,7,8-hexahydro-2H-1,4-benzoxazinyl, 3,4,5,6,7,8-hexahydro-2H-1,4-benzothiazinyl, 9-azabicyclo[3.3.1]non-9-yl, 1-azepan-1-yl, 2,8-diazaspiro[4.5]dec-8-yl, octahydroisoindol-2-yl, 4-azatricyclo[5.2.1.0$^{2,6}$]dec-4-yl, 3-azabicyclo[3.2.1]oct-3-yl, 3,7-diazabicyclo[3.3.1]non-3-yl, 3-azabicyclo[3.3.1]non-3-yl, 8-azabicyclo[3.2.1]oct-8-yl, 3-azabicyclo[3.2.2]non-3-yl, 2,3,4,5-tetrahydro-1H-1-benz[6,7-b]azepinyl and 5,6-dihydrophenanthridinyl.

5. A pharmaceutical preparation comprising, as an active pharmaceutical ingredient, a compound according to claim 1 in free form or as a pharmaceutically usable salt, and a pharmaceutically acceptable excipient.

6. A method for the treatment of a condition selected from the group consisting of hypertension, heart failure, glaucoma, cardiac infarction, kidney failure and restenosis, said method comprising administering a compound according to claim 1, or a salt or prodrug thereof, to a patient in need thereof.

7. A pharmaceutical preparation comprising, as an active pharmaceutical ingredient, a compound according to claim 2 in free form or as a pharmaceutically usable salt, and a pharmaceutically acceptable excipient.

8. A pharmaceutical preparation comprising, as an active pharmaceutical ingredient, a compound according to claim 3 in free form or as a pharmaceutically usable salt, and a pharmaceutically acceptable excipient.

9. A pharmaceutical preparation comprising, as an active pharmaceutical ingredient, a compound according to claim 4 in free form or as a pharmaceutically usable salt, and a pharmaceutically acceptable excipient.

* * * * *